(12) United States Patent
Krasnow et al.

(10) Patent No.: US 10,765,361 B2
(45) Date of Patent: Sep. 8, 2020

(54) AUTOMATED SEQUENTIAL INJECTION AND BLOOD DRAW

(71) Applicant: Verily Life Sciences LLC, Mountain View, CA (US)

(72) Inventors: Benjamin David Krasnow, Redwood City, CA (US); Eric Peeters, San Jose, CA (US); Peter Howard Smith, Pacifica, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 321 days.

(21) Appl. No.: 14/635,580

(22) Filed: Mar. 2, 2015

(65) Prior Publication Data

US 2016/0256106 A1 Sep. 8, 2016

(51) Int. Cl.
*A61B 5/00* (2006.01)
*A61B 5/15* (2006.01)
(Continued)

(52) U.S. Cl.
CPC .......... *A61B 5/4839* (2013.01); *A61B 5/1411* (2013.01); *A61B 5/1455* (2013.01);
(Continued)

(58) Field of Classification Search
CPC ................ A61B 5/4839; A61B 5/1411; A61B 5/150068; A61B 5/150099;
(Continued)

(56) References Cited

U.S. PATENT DOCUMENTS

| 4,031,889 A | 6/1977 | Pike |
|---|---|---|
| 4,243,036 A | 1/1981 | Ott |

(Continued)

FOREIGN PATENT DOCUMENTS

| CN | 103100128 A | 5/2013 |
|---|---|---|
| GB | 2414186 A | 11/2005 |

(Continued)

OTHER PUBLICATIONS

Cunningham, D.D., et al., "Blood Extraction from lancet wounds using vacuum combined with skin stretching," J Appl Physiol, vol. 92, p. 1089-1096 (2002).

(Continued)

*Primary Examiner* — Kevin C Sirmons
*Assistant Examiner* — Alexandra Lalonde
(74) *Attorney, Agent, or Firm* — McDonnell Boehnen Hulbert & Berghoff LLP

(57) ABSTRACT

Devices are provided to automatically inject drugs or other payloads into or beneath skin. These devices include an injector configured to drive a hollow needle into the skin and subsequently to deliver the payload through the hollow needle. Applied suction acts to draw blood from the puncture formed in the skin through the hollow needle, into the device, and to a sensor, blood storage element, or other payload. In some examples, the blood is drawn through the hollow needle when the hollow needle is penetrating the skin. In some examples, these devices are additionally configured to retract the hollow needle from the skin and/or to perform some other functions. These devices can be wearable and configured to automatically access blood or deliver a payload into skin, for example, to operate at one or more points in time while a wearer of a device is sleeping.

8 Claims, 11 Drawing Sheets

(51) Int. Cl.
| | |
|---|---|
| *A61B 5/151* | (2006.01) |
| *A61M 5/20* | (2006.01) |
| *A61B 5/1455* | (2006.01) |
| *A61B 5/155* | (2006.01) |
| *A61B 5/157* | (2006.01) |
| *A61B 17/34* | (2006.01) |
| *A61M 5/00* | (2006.01) |
| *A61M 5/32* | (2006.01) |

(52) U.S. Cl.
CPC .............. *A61B 5/155* (2013.01); *A61B 5/157* (2013.01); *A61B 5/1513* (2013.01); *A61B 5/1519* (2013.01); *A61B 5/150022* (2013.01); *A61B 5/150068* (2013.01); *A61B 5/150099* (2013.01); *A61B 5/15109* (2013.01); *A61B 5/15125* (2013.01); *A61B 5/15194* (2013.01); *A61B 5/150236* (2013.01); *A61B 5/150343* (2013.01); *A61B 5/150389* (2013.01); *A61B 5/150519* (2013.01); *A61B 5/150572* (2013.01); *A61B 5/150854* (2013.01); *A61B 5/150969* (2013.01); *A61B 5/681* (2013.01); *A61B 5/686* (2013.01); *A61B 17/3468* (2013.01); *A61M 5/007* (2013.01); *A61M 5/20* (2013.01); *A61M 5/2033* (2013.01); *A61M 5/2046* (2013.01); *A61M 5/2053* (2013.01); *A61M 5/3287* (2013.01); *A61M 2005/206* (2013.01)

(58) Field of Classification Search
CPC ........ A61B 5/150236; A61B 5/150519; A61B 5/150969; A61B 5/681; A61B 5/157; A61B 10/0045; A61B 17/3468; A61B 5/15107; A61B 5/155; A61B 5/150412; A61B 5/150503; A61B 5/150572; A61B 5/15109; A61B 5/15125; A61B 5/15144; A61B 5/150351; A61B 5/1509; A61B 2017/3419; A61B 2017/3441; A61B 1/00137; A61B 5/150206; A61B 5/150213; A61B 5/150251; A61B 5/150534; A61B 5/150541; A61M 5/2053; A61M 5/3287; A61M 2005/206; A61M 2005/14252; A61M 5/14248; A61M 2005/14256; A61M 2005/1426; A61M 5/1723; A61M 5/2046
See application file for complete search history.

(56) References Cited

U.S. PATENT DOCUMENTS

| | | | |
|---|---|---|---|
| 4,547,189 A | 10/1985 | Moore, Jr. | |
| 4,684,366 A | 8/1987 | Denny et al. | |
| 4,684,436 A | 8/1987 | Burns et al. | |
| 4,758,232 A | 7/1988 | Chak | |
| 4,787,398 A | 11/1988 | Garcia et al. | |
| 4,886,499 A * | 12/1989 | Cirelli | A61M 5/142 604/131 |
| 5,636,640 A | 6/1997 | Staehlin | |
| 5,662,127 A | 9/1997 | De Vaughn | |
| 6,045,534 A * | 4/2000 | Jacobsen | A61M 5/14248 604/140 |
| 6,340,354 B1 | 1/2002 | Rambin | |
| 6,695,860 B1 * | 2/2004 | Ward | A61B 5/00 600/505 |
| 6,896,666 B2 * | 5/2005 | Kochamba | A61M 5/14248 604/141 |
| 7,001,344 B2 | 2/2006 | Freeman et al. | |
| 7,806,867 B2 | 10/2010 | Willis et al. | |
| 8,808,202 B2 * | 8/2014 | Brancazio | A61B 5/1411 600/576 |
| 9,039,638 B2 | 5/2015 | Arnitz | |
| 9,113,836 B2 | 8/2015 | Bernstein et al. | |
| 9,295,417 B2 | 3/2016 | Haghgooie et al. | |
| 9,380,972 B2 | 7/2016 | Fletcher et al. | |
| 9,408,568 B2 | 8/2016 | Fletcher et al. | |
| 2002/0040208 A1 * | 4/2002 | Flaherty | A61M 5/14248 604/288.01 |
| 2003/0088191 A1 * | 5/2003 | Freeman | A61B 5/15142 600/583 |
| 2004/0116865 A1 * | 6/2004 | Bengtsson | A61M 5/14248 604/171 |
| 2004/0133126 A1 | 7/2004 | McNenny | |
| 2007/0213638 A1 | 9/2007 | Herbrechtsmeier et al. | |
| 2007/0213682 A1 | 9/2007 | Haar et al. | |
| 2009/0105614 A1 * | 4/2009 | Momose | A61B 10/0045 600/583 |
| 2009/0124876 A1 | 5/2009 | Nakamura et al. | |
| 2009/0149809 A1 * | 6/2009 | Bollenbach | A61M 5/2033 604/111 |
| 2010/0274202 A1 | 10/2010 | Hyde et al. | |
| 2011/0217762 A1 * | 9/2011 | Viator | G01N 21/1702 435/287.1 |
| 2012/0022499 A1 * | 1/2012 | Anderson | A61M 5/14248 604/506 |
| 2012/0039809 A1 * | 2/2012 | Levinson | A61B 10/0045 424/9.1 |
| 2012/0271123 A1 | 10/2012 | Castle et al. | |
| 2014/0073992 A1 | 3/2014 | Hufford et al. | |
| 2014/0296777 A1 * | 10/2014 | Haitsuka | A61M 5/30 604/70 |
| 2016/0354555 A1 * | 12/2016 | Gibson | A61M 5/40 |

FOREIGN PATENT DOCUMENTS

| | | |
|---|---|---|
| WO | 0205890 A2 | 1/2002 |
| WO | 2010122222 A2 | 10/2010 |
| WO | 2013/182858 | 12/2013 |

OTHER PUBLICATIONS

Wang, Y., et al., "Electrochemical Sensors for Clinic Analysis," Sensors, vol. 8, p. 2043-2081 (2008).
International Search Report of International Application No. PCT/US2016/015955 dated Jun. 2, 2016.
International Search Report and Written Opinion of International Application No. PCT/US2016/015955 dated Aug. 8, 2016.
International Search Report and Written Opinion for PCT/US2016/016367 dated Aug. 4, 2016.
"Invitation to Pay Additional Fees and, Where Applicable, Protest Fee" prepared by International Searching Authority (EPO), dated May 30, 2016, issued in connection with International Application No. PCT/US2016/016367, filed Feb. 3, 2016, 6 pages.
International Search Report of International Application No. PCT/US2016/015955 dated Aug. 8, 2016.

* cited by examiner

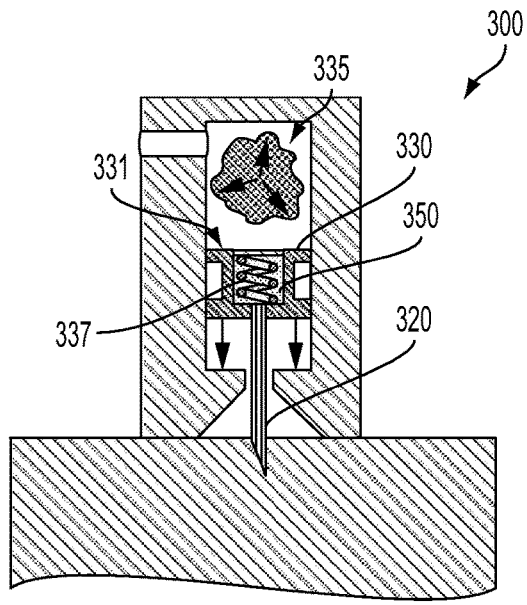
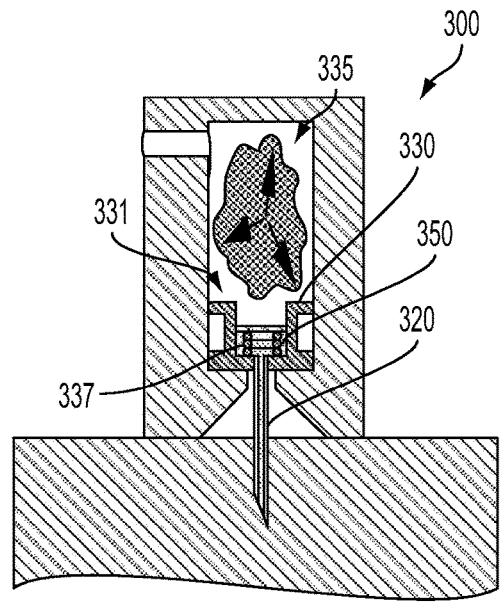
FIG. 3A  FIG. 3B
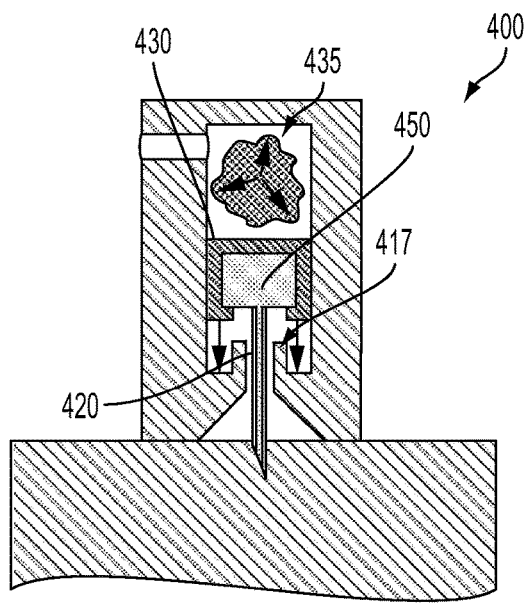
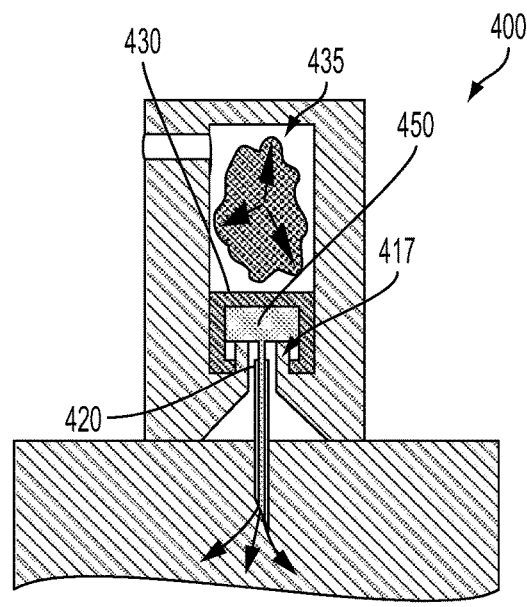
FIG. 4A  FIG. 4B

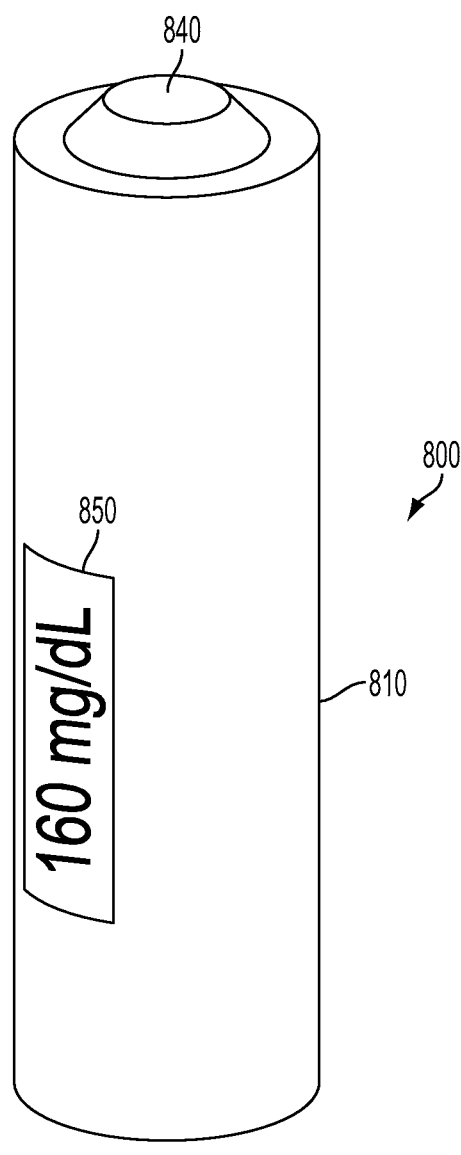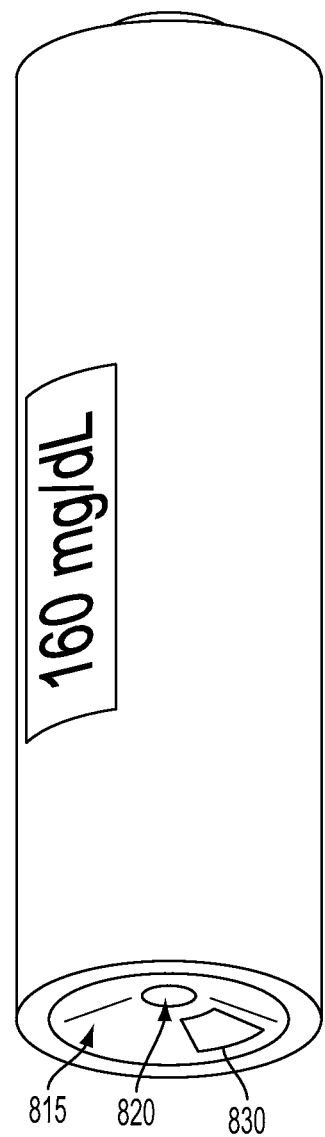
FIG. 8A
FIG. 8B

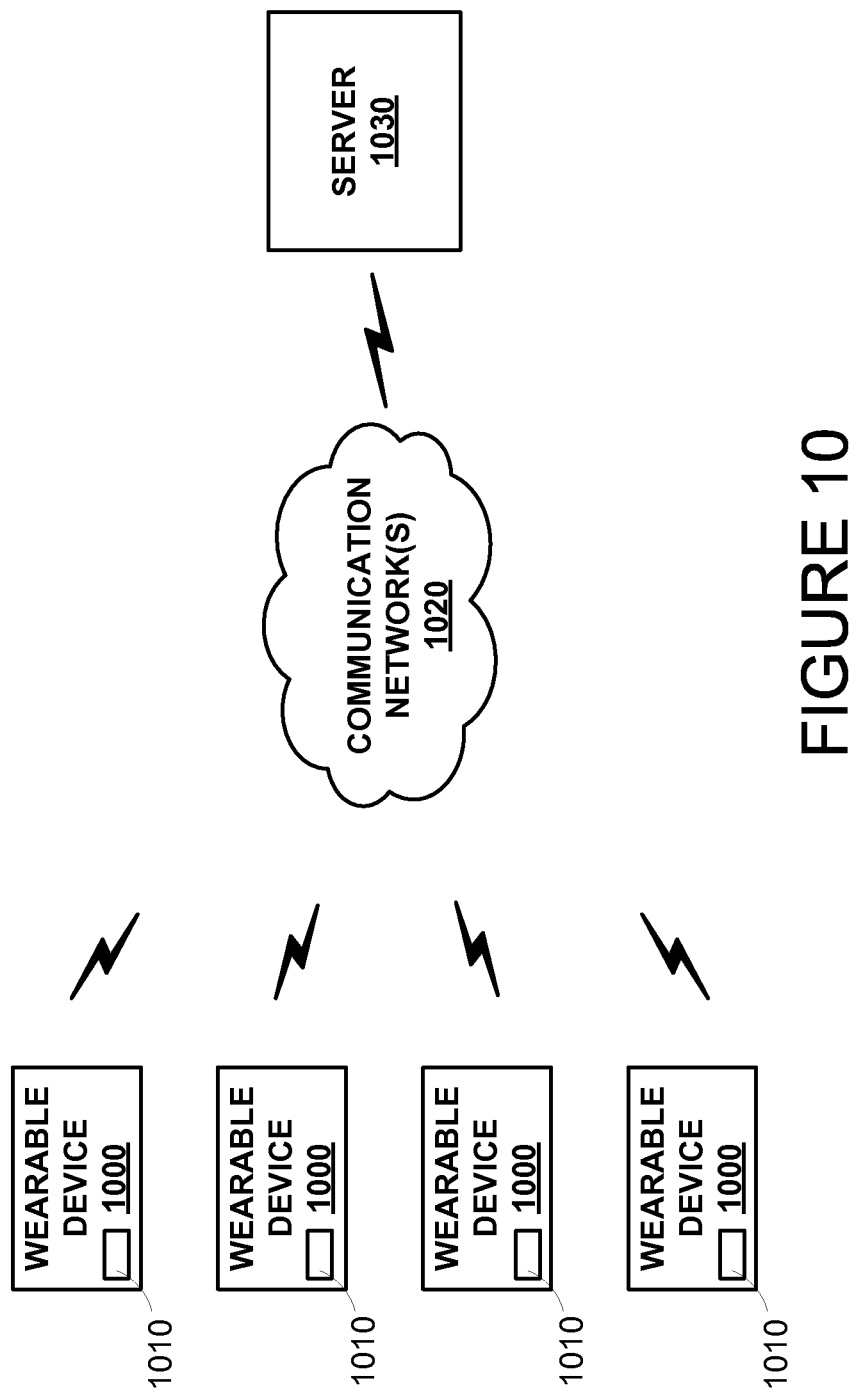

AUTOMATED SEQUENTIAL INJECTION AND BLOOD DRAW

BACKGROUND

Unless otherwise indicated herein, the materials described in this section are not prior art to the claims in this application and are not admitted to be prior art by inclusion in this section.

Certain medical states or conditions of a human body can be detected by detecting one or more properties of blood in the body. In some examples, such medical states can be detected by extracting a sample of the blood from the body and detecting the one or more properties of the extracted blood using a sensor or other system external to the body. For example, a lancet or other skin-penetrating device could be used to penetrate the skin such that blood is emitted from the skin and/or such that blood can be caused to be emitted from the skin. In another example, a needle, tubing, and other equipment could be used to access blood in an artery or vein of a body. Blood accessed from a body can be exposed to a sensor (e.g., a sensor placed in contact with blood at the surface of skin that has been penetrated). Additionally or alternatively, accessed blood can be stored for later analysis. In a particular example, a lancet can be used to penetrate skin, allowing blood to be emitted from the skin such that a blood glucose level of the blood can be measured using an electrochemical sensor placed in contact with the emitted blood.

SUMMARY

Some embodiments of the present disclosure provide a system including: (i) a hollow needle having a first end that is configured to penetrate skin; (ii) a reservoir that contains a payload; (iii) an injector configured to drive the hollow needle into the skin to form a puncture in the skin, to deliver the payload from the reservoir into the skin via the hollow needle, and to retract the hollow needle from the skin; and (iv) a suction source configured to draw blood from the formed puncture in the skin into the system.

Some embodiments of the present disclosure provide a system including: (i) penetrating means containing a channel and having a first end that is configured to penetrate skin; (ii) reservoir means that contain a payload; (iii) injector means configured to drive the penetrating means into the skin to form a puncture in the skin, to deliver the payload from the reservoir means into the skin via the channel of the penetrating means, and to retract the penetrating means from the skin; and (iv) suction means configured to provide suction to draw blood from the formed puncture in the skin into the system.

Some embodiments of the present disclosure provide a method including: (i) mounting a wearable device to skin, where the wearable device includes: (a) a hollow needle having a first end that is configured to penetrate skin, (b) a reservoir, wherein the reservoir contains a payload, (c) an injector, and (d) a controller configured to operate the injector; and (ii) operating the injector, using the controller, to drive the hollow needle into the skin to form a puncture in the skin and to deliver the payload into the skin through the channel.

Some embodiments of the present disclosure provide a wearable device including: (i) a hollow needle having a first end that is configured to penetrate skin; (ii) a reservoir that contains a payload; (iii) an injector configured to drive the hollow needle into the skin to form a puncture in the skin and to deliver the payload from the reservoir into the skin through the hollow needle; and (iv) a controller configured to operate the injector to drive the hollow needle into the skin and to deliver the payload into the skin via the channel.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3A is a cross-sectional view of an example device mounted to a skin surface when a needle of the example device is piercing the skin.

FIG. 3B is a cross-sectional view of the example device of FIG. 3A when the fluid contained in the example device is being delivered into the skin.

FIG. 4A is a cross-sectional view of an example device mounted to a skin surface when a needle of the example device is piercing the skin.

FIG. 4B is a cross-sectional view of the example device of FIG. 4A when the fluid contained in the example device is being delivered into the skin.

FIG. 8A is a perspective top view of an example handheld body-mountable device.

FIG. 8B is a perspective bottom view of the example handheld body-mountable device shown in FIG. 8A.

FIG. 10 is a block diagram of an example system that includes a plurality of wearable devices in communication with a server.

DETAILED DESCRIPTION

Figure 1A:
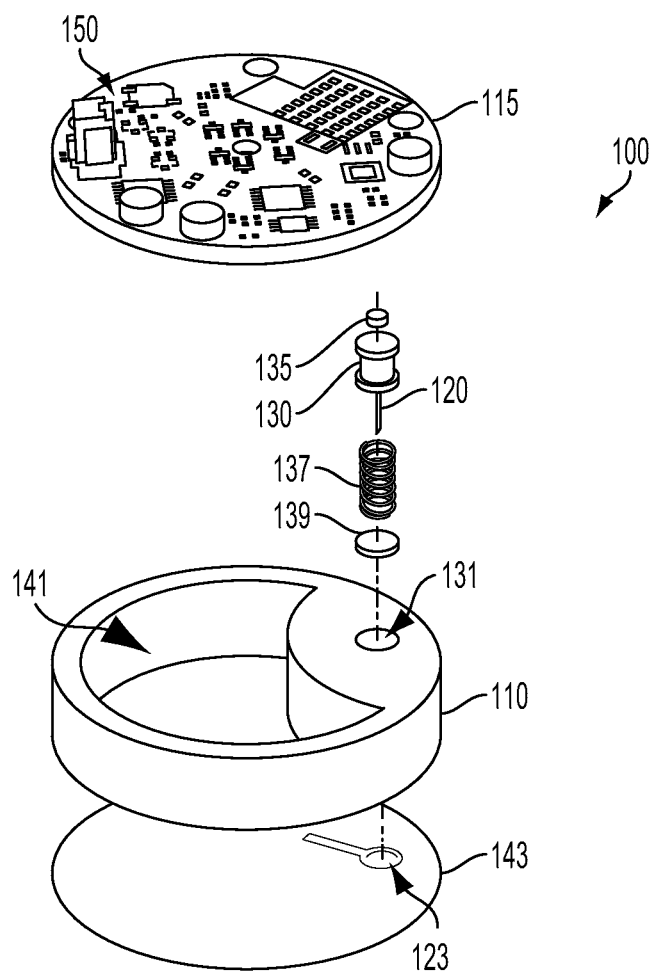
FIG. 1A is an exploded view of an example device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of a device to inject a fluid or other materials into and/or to extract a fluid from an environment of interest by piercing a barrier and/or penetrating an element within the environment of interest is desired. The environment may be or include any living or non-living body or a portion thereof, a gel, an emulsion, a fluid conduit, a fluid reservoir, an ampoule or other container containing a drug, an egg, etc.

I. OVERVIEW

A handheld, body-mountable, wearable, desktop, or otherwise-configured device may be configured to deliver fluids, drugs, inoculants, vaccines, nano- or micro-particles, microelectronics, or other materials or payloads into a living body (or to insert some other payload into some other environment of interest). Such a device could include means for penetrating or piercing the skin to allow the payload to be delivered into the skin. Such penetrating or piercing means could include one or more hollow needles driven into the skin by an injector incorporating chemical propellants, mechanical or electromechanical elements, or some other elements or components configured to drive the one or more hollow needles into the skin and/or to deliver the payload into the skin via one or more punctures or other penetrations in the skin formed by the one or more hollow needles.

Fluids, drugs, vaccines, nano- or micro-particles, microelectronics, or other payloads could be delivered, using embodiments described herein, for a variety of applications. Pharmaceuticals could be delivered to treat, manage, or otherwise affect a health state or condition of a person. For example, the person could have diabetes and the delivered fluid could include insulin or some other substance(s) configured to control a blood sugar level of the person. Contrast agents or other substances (e.g., nano- or micro-particles) could be delivered to facilitate imaging of structures of a person's body, to allow detection of an analyte in the body (e.g., to detect cancer cells in the person's body), to collect an analyte in the person's body for elimination (e.g., via the kidneys, via application of RF or other energies to the person's body) and/or extraction (e.g., using an embodiment herein configured to access and detect, collect, or otherwise interact with blood from a person's body), or to facilitate some other application. In some examples, payloads composed of solids, gels, emulsions, polymers, or other materials or objects could be delivered into a person's body in addition to or alternative to fluids. For example, a sliver of a drug-eluting polymer, microelectronics including a biosensor, or some other payload could be delivered into skin using embodiments described herein.

An injector or other means configured to drive one or more hollow needles or other means for penetrating skin could be configured in a variety of ways to provide a force to drive the one or more hollow needles into the skin and subsequently to deliver fluids (or some other payload) into the skin through the hollow needle(s). For example, the injector could include a piston disposed in a chamber and to which the one or more needles are coupled; a propellant could be used to apply pressure behind the piston to drive the piston, and attached one or more needles, forward such that the one or more needles are driven into the skin. A spring or some other means could also be provided to apply a force to retract the one or more needles subsequent to being driven into the skin. In a particular example, the propellant could include a chemical or other material (e.g., nitrocellulose) that could be ignited (e.g., by being heated to an ignition temperature by, e.g., a resistive heating element) to produce gases that could apply pressure on the piston to drive the needle into skin. In another example, the propellant could include compressed gases introduced into the chamber (e.g., by opening a valve, by puncturing a seal, by electrochemically generating the gases, by chemically generating the gases) and the compressed gases could apply pressure on the piston to drive the needle into skin. Additionally or alternatively, an injector could include preloaded springs, magnetic elements coupled to cams, motors, solenoids, ultrasonic vibrators, or other elements configured to drive one or more needles into skin.

The injector could additionally be configured to apply a force to a reservoir containing the payload (e.g., a drug-containing fluid) or could be configured in some other way to deliver the payload, through the hollow needle, into skin. For example, a spring, expanding propellant gas, or some other force-generating means could apply pressure on such a reservoir. Additionally or alternatively, a device could include a stop or some other means configured to arrest the motion of the hollow needle and/or reservoir as the hollow needle and/or reservoir move toward the skin to drive the hollow needle into the skin, and a driving mass or other means could apply a force to the reservoir related to the arrest of the hollow needle and/or reservoir such that the fluid is delivered, through the hollow needle, into skin. In some examples, the injector could act to couple the channel of the hollow needle with a fluid-containing reservoir (e.g., a reservoir containing a payload fluid under pressure) by opening a valve, moving the needle and/or reservoir relative to each other such that they are coupled, breaching a seal, or by some other coupling means. Other means (e.g., application of suction, e.g., from a suction source of the device, chemical reactions, direction of fluids using hydrophobic/hydrophilic surface coatings and/or wicking elements) to deliver fluids or other payloads into skin via a hollow needle are anticipated.

Such a payload-delivering device could additionally include suction means for applying suction to draw blood into the device to be measured, detected, collected, stored, or otherwise used for some application (e.g., to draw blood into a collection chamber of the device). For example, such a blood-accessing device could include a sensor configured to detect glucose in blood received by the device from the skin. Such suction could be applied to a seal and driving a needle into skin could include driving the needle through the seal, exposing the skin to the suction such that the suction draws blood from the skin, through the formed one or more holes in the seal, into the device (e.g., to a sensor, blood collection element, or other component(s) of the device). Additionally or alternatively, suction could be applied through the hollow needle to draw blood into the device, through the hollow needle, when the needle is penetrating the skin. A body-mountable blood-accessing device could include multiple needles, injectors, seals, suction sources, sensors, blood storage elements, or other components such that the body-mountable blood-accessing device could be operated to automatically access blood from a wearer at a number of specified points in time, e.g., while the wearer sleeps.

In some examples, devices as described herein could receive, draw, and/or interact with blood emitted from the skin through some means alternative or additional to one or more suction sources, e.g., by including hydrophobic and/or hydrophilic coatings, by including one or more capillary tubes or other elements configured to wick the blood, or through some other means. Additionally or alternatively, a sensor, blood storage element, or other component(s) of the device could be located proximate to the puncture formed in the skin by the needle such that blood emitted from the blood comes into contact with the sensor, blood storage element, or other component(s) of the device.

A suction source or other suction means configured to provide suction to skin, to a seal, and/or to some other elements to draw blood into a device and/or to draw blood into a device by some other means (e.g., through a hollow needle) could provide suction by a variety of mechanisms. In some examples, the suction source could include a pump, an endobaric chemical process, a spring-loaded volume, or some other actuated element(s) configured to be operated to reduce a pressure to which the seal is exposed or to otherwise provide suction to the seal. In some examples, the suction source could include an evacuated volume, i.e., an enclosed volume having a lower pressure than the atmosphere surrounding the device such that, when the seal is breached, blood (or some other fluid or material) is drawn through/toward the one or more holes in the seal.

Such suction provided to skin could act to draw the skin toward the device (e.g., toward one or more holes formed in a seal of the device, e.g., by being pierced by a needle of the device). In some examples, the device could include a concave depression (e.g., a spherical dome depression) formed in a seal and/or in some other element(s) of the device such that the suction provided by the suction source could draw a portion of the skin into the concave depression. Such displacement of the skin could act to increase a rate and/or duration of the emission of blood from the skin. A blood-accessing device could additionally or alternatively be configured in other ways to increase the rate and/or duration of the emission of blood from the skin following penetration by one or more needles. In some examples, heparin or some other anti-clotting or anti-coagulating substance could be introduced on/in the skin (e.g., by being deposited and/or injected by the one or more hollow needles). In some examples, an amount of blood flow in the skin could be increased by, e.g., applying suction to the skin (e.g., using the same or a different suction source as is used to drawn blood into the device), applying a fictive force to the skin (e.g., by rubbing the skin), and/or heating the skin before driving the one or more hollow needles into the skin.

Blood accessed by devices as described herein (e.g., by driving one or more hollow needles into skin and receiving blood emitted from the puncture formed in the skin by the hollow needles) could be used for a variety of applications. In some examples, the device could contain a sensor that could be configured to detect one or more properties of the blood (e.g., to detect the concentration of an analyte in the blood). Sensors could be configured to detect glucose, blood cell counts, electrolytes, hormones, cholesterol, or some other analytes in accessed blood. Additionally or alternatively, devices as described herein could be configured to store accessed blood for later use, e.g., for interrogation by sensors or other elements of some other devices or systems. Storing blood could include providing heparin or other stabilizing and/or anti-clotting agents such that the blood is stored as a fluid. Additionally or alternatively, accessed, stored blood could be allowed to dry, clot, coagulate, or engage in some other process, and the dried or otherwise altered stored blood could be presented to a sensor device configured to receive the stored blood. In some examples, one or more blood-storing elements of a blood-accessing device could be removable, and could be removed from the device to be presented to another system for analysis (e.g., the removable blood-storing aspects of the device could be removed and sent to a centrally located laboratory).

In some examples, a device may include a user interface that is configured to provide user-discernible indications (e.g., visual, audible, and/or tactile indications) of the operation of the device to deliver fluids or other payloads into skin and/or information about blood accessed by the device and sensed by sensors of the device, progress or other information related to a function of the device, or other information. In some examples, the user interface could additionally provide a means for one or more settings of the device (e.g., timing of one or more future activations of the device to deliver fluids or other payloads into skin, a user information privacy setting, a user's credentials to access a service) to be specified by a user according to the user's preferences. In some examples, the device may include a wireless communication interface that can transmit/receive data to/from an external device, for example, using Bluetooth, ZigBee, WiFi, and/or some other wireless communication protocol. The data transmitted by the wireless communication interface may include data indicative of one or more physiological parameters or health state measured and/or determined based on blood accessed by the device. The wireless communications interface could additionally or alternatively be configured to receive data from an external system.

It should be understood that the above embodiments, and other embodiments described herein, are provided for explanatory purposes, and are not intended to be limiting. Further, the terms 'access,' 'accessed,' 'accessing,' and any related terms used in relation to the operation of a device to induce emission of blood from skin are used herein (unless otherwise specified) to describe any operation or configuration of a device or system to receive blood from skin or from some other tissue. This could include receiving blood that has been emitted from skin in response to cutting, piercing, incising, cutting, or otherwise penetrating the skin. This could include actively pulling, wicking, suctioning, or otherwise drawing such emitted blood from the skin and/or form the surface of the skin into the device and/or toward some sensor, storage element, or other element(s) of the device. The term "payload" and any related terms used in relation to the operation of a device to deliver a fluid, gel, solid, manufactured object, or other material or materials into or through skin are used herein (unless otherwise specified) to describe any fluids, gels, hydrogels, emulsions, drugs, vaccines, inoculants, micro- or nano-particles, microelectronics, polymers, or other materials or combinations of materials that could be delivered, though a hollow needle, into or through skin or into or through some other environment of interest.

Embodiments as described herein could provide all or any subset of the functionalities described herein. For example, a device could be configured to penetrate skin with a hollow needle and to deliver a fluid or other payload into the skin through the hollow needle. In another example, such a device could additionally be configured to retract the hollow needle from the skin subsequent to delivering the payload into the skin. In yet another example, a device could be configured to penetrate skin with a hollow needle, to deliver a fluid or other payload into the skin through the hollow needle, and to detect one or more properties of and/or to collect blood emitted from the skin in response to being pierced by the hollow needle.

Further, while examples and embodiments described herein refer to delivering fluid or other payloads into skin and/or accessing blood from skin, it should be understood that methods, devices, and other embodiments described herein could be employed to deliver payloads to and/or access other fluids from other environments of interest.

II. EXAMPLE OPERATION OF DEVICES TO DELIVER SUBSTANCES INTO SKIN

A device could be configured in a variety of ways to deliver a fluid, material, manufactured device or object, or some other payload into skin or into some other tissue or environment. Such a device could include a variety of penetrating means (e.g., one or more hollow needles) configured to be driven into the skin by injecting means (e.g., by a piston and a chemical propellant) such that fluids or other payloads can be delivered by delivery means, through the hollow needle, from a reservoir or other storage volume/element(s) into the skin. In some examples, the delivery means could be part of the injecting means, e.g., an expanding propellant gas could act to drive the hollow needle into the skin and to apply a force on a reservoir to deliver fluid or some other payload through the hollow needle into the skin. The device could additionally include means (e.g., part of the injecting means) to subsequently retract the hollow needle from the skin (e.g., by force applied by a spring). In some examples, blood can be emitted from the resultant wound (e.g., puncture) in the skin, and the emitted blood could be drawn into, collected by, or otherwise interacted with by the device for a variety of applications. Toward such ends, devices could include a variety of means (e.g., suction sources, seals, channels, concave depressions) configured to draw blood out of the skin (e.g., through the hollow needle, through a hole in a seal of the device), to draw blood emitted from the skin into the device, and/or to direct such accessed blood toward one or more sensors, blood storage elements, or other elements of the device. Further such devices could include additional elements, sensors, controllers, user interfaces, power sources, communications interfaces or other elements according to an application.

Such devices could be configured to be used to penetrate, pierce, deliver payloads into, access, detect, store, or otherwise interact with blood from, or otherwise interact with skin or other elements of a body in a variety of ways. In some examples, such devices could be configured to be mounted to skin or otherwise worn such that the device can inject payloads into skin and/or access blood automatically, e.g., a controller or other element(s) of the device could operate an injector of the device to pierce the skin and deliver payloads and/or access blood while a wearer of the device sleeps. Alternatively, the device could be a handheld device configured to be manually mounted to a portion of skin and operated to deliver a payload and/or access blood from the skin. In some examples, the device could be wall-mounted, situated on a desktop, or disposed or mounted in some other way, and mounting the device to skin could include positioning an arm or other aspect of a body proximate to the device (e.g., positioning skin of the wrist of a person proximate to a specified aspect of the device). In some examples, one or more elements (e.g., injectors, needles, reservoirs, seals, suction sources, sensors, blood storage elements) could be removable from the device, e.g., such that other elements of the device (e.g., controllers, user interfaces, mounts) could be reusable by replacing used removable elements of the device.

The payload could include a variety of fluids, liquids, gels, emulsions, hydrogels, solid elements, particles, compounds, microelectronic elements, compounds, drugs, pharmaceuticals, vaccines, cells, and/or other materials or combinations of materials. In some examples, one or more aspects of the payload (e.g., microparticles, nanoparticles, rigid components, microelectronic components, cells, micelles) could be disposed in a carrier fluid of the payload. The carrier fluid of the payload could be configured to reduce a friction of other elements of the payload as the other elements are delivered from the device, through the hollow needle and into the skin. The carrier fluid could be configured to transmit a force or pressure exerted on a reservoir to the other elements of the payload to facilitate delivery of the other elements into the skin. The carrier fluid could include drugs (e.g., heparin) or other substances (e.g., an adhesive to maintain an electronic biosensor of the payload in the skin once delivered) or could be configured in some other way to provide other functions. In some examples, a viscosity, density, degree of shear thickening, or other properties of the payload could be controlled by adding substances to a fluid of the payload. For example, a gelling agent could be added to a fluid of the payload. Gelling agents could include hydrogel-forming polymers or monomers, superabsorbent materials, gelatin, proteins, or other materials that, when added to the fluid of the payload, increase a viscosity or density of the fluid of the payload.

Fluids, drugs, vaccines, inoculants, devices, electronics, objects, or other payloads delivered into skin using devices and methods disclosed herein could be configured in a variety of ways and used for a variety of applications. The volume of a fluid (or other material) delivered can be related to the configuration of the device. The device could be configured (e.g., a stroke length, a force applied to a reservoir and/or a compliance of materials composing the reservoir, a viscosity of a fluid payload and/or carrier fluid of the payload contained in the reservoir, a diameter of the channel in one or more hollow needles) to deliver a specified minimum amount of the payload according to an application of the device. For example, the device could be configured to deliver a sufficient amount of a drug-containing fluid payload to effect a specified change in the function of a person's body (e.g., to control a blood sugar level of the person's body). In another example, the device could be configured to deliver fluids or other payloads (e.g., a microelectronic biosensor or some other electronic device) to a specified location or layer within or beneath the skin, e.g., a length of a hollow needle and/or a stroke length of the motion of the hollow needle into the skin when driven by an injector could be specified to deliver a payload to the subcutaneous layer beneath skin.

Blood accessed using devices and methods disclosed herein could be used for a variety of applications. Such applications could include any applications where one or more properties of a person and/or of blood of the person can be detected or determined from a volume of blood accessed using such devices. The volume of blood can be related to the configuration of the device, and could be between approximately one and approximately 10 microliters. For example, the device could be configured to access (e.g., to penetrate the skin and to apply suction to the skin to draw) more than approximately 3 microliters of blood and to detect the concentration of one or more analytes (e.g., glucose, hormones, blood cells) in the accessed blood. The device could be configured (e.g., a stroke length, diameter or shape of a needle, the shape of a concave depression into which skin could be drawn by suction, an amount of applied suction) to provide a specified minimum amount of blood according to a property of the blood to be measured and/or a sensor used to detect such a property. For example, the device could be configured to access sufficient blood to allow detection of a glucose level of the blood using an electrochemical sensor disposed in the device. In another example, the device could be configured to access and store a sufficient amount of blood to allow detection of a property of the blood by some other device or system that is provided with the stored blood from the blood-accessing device.

Figure 1B:
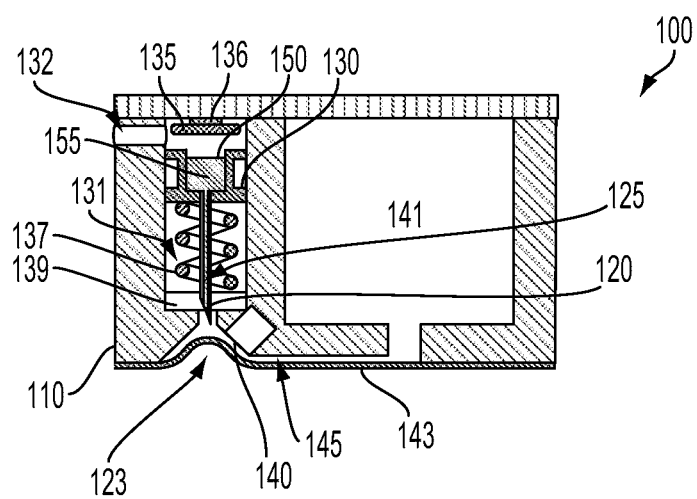
FIG. 1B is a cross-sectional view of the example device of FIG. 1A.

An example of such a payload-delivering and blood-accessing device is illustrated in FIGS. 1A and 1B. FIG. 1A shows an expanded perspective view of components of the device. FIG. 1B is a cross-sectional view of the device 100 illustrating in detail elements of the device 100. The device 100 includes a housing 110 that is formed to include a chamber 131 and an evacuated volume 141 as well as other features. The device 100 could be used on its own (e.g., by placing a bottom surface of the device 100 in contact with skin), could be part of another device (e.g., part of a wrist-mountable or otherwise body-mountable device), could be a removable module of another device, or could be configured or operated in some other way.

The device 100 includes a number of elements disposed within the chamber 131 formed in the housing 110. The chamber 131 is shown as a cylindrical shape formed in the housing, but could assume other shapes according to an application. The chamber contains a hollow needle 120 (i.e., a needle formed to have a contained needle channel 125 along its length) configured to penetrate skin. A piston 130 is coupled to the needle 120 and configured to slidably move within the chamber 131 (e.g., along the long axis of the chamber 131). A reservoir 150 containing a payload 155 (for example, a drug-containing fluid, gel, or hydrogel) is formed in the piston 130 and coupled to the needle channel 125 within the hollow needle 120. The chamber 131 additionally contains a propellant 135 configured (a) to slidably move the piston 130 within the chamber 131 to drive the needle 120 into skin, (b) to drive the needle 120 through a seal 143 disposed on a bottom surface of the housing 110, and (c) to apply a force to reduce a volume of the reservoir (e.g., by collapsing and/or displacing one or more elements of the reservoir) such that the payload 155 is delivered from the reservoir 150 through the needle channel 125 and into skin that is penetrated by the hollow needle 120.

The chamber additionally contains a spring 137 configured to retract the needle 120 from the skin, a sealant layer 139 that is configured to be pierced by the hollow needle 120 and a resistive element 136 configured to ignite the propellant 135 by providing sufficient heat to the propellant 135 when current passes through the resistive element 136. The top of the chamber 131 is closed by a circuit board 115 or other member bonded or otherwise adhered to the housing 110. Electronics 150 (e.g., one or more controllers, logic gates, current sources, electronic switches, radio transceivers, analog-to-digital converters) disposed on the circuit board 115 could be configured to perform operations of the device 100, e.g., to apply current to the resistive element 136 (or to other resistive elements or to operate other components of other injectors of the device 100) to ignite the propellant 135 at a specified point in time, to operate a sensor to detect a property of blood accessed from skin by the device 100, or to perform some other operations according to an application.

A hole is formed in the bottom of the chamber 131 through the housing 110 such that the hollow needle 120 can be driven into skin proximate the bottom of the housing 110. A chamber vent 132 is formed in the housing 110 to allow gases produced by the ignition of the propellant 135 to be vented out of the device such that the spring 137 can retract the hollow needle 120 subsequent to the ignited propellant 163 causing the piston 130 to drive the hollow needle 120 through the seal 143 and into skin. The diameter, number, geometry, and other properties of the vent 132 and or additional vents formed in components of the device 100 (e.g., through the piston, through the wall of the chamber 131 at additional or alternative locations) could be specified to control a force with which the piston 130 drives the hollow needle 120, a duration of time during which the hollow needle 120 penetrates skin before being retracted by the spring 137, or other properties of operation of the device 100.

The seal 143 includes a concave depression 123 through which the hollow needle 120 penetrates the seal 143 to form a hole in the seal 143 when driven downward by the piston 130. A channel 145 is formed above the concave depression 123 behind the seal 143 and connecting the region behind the seal 143 with an evacuated volume 141 formed in the housing 110. The top of the evacuated volume 141 is sealed by the circuit board 115. Atmospheric gases are prevented from entering the evacuated volume 143 through the chamber 131 by the sealant layer 139 and prevented from entering the evacuated volume 141 through the bottom of the housing 110 (e.g., through the concave depression 123) by the seal 143. A sensor 140 is contained within the channel 145 proximate the concave depression 123. The pressure in the evacuated volume 141 is sufficiently lower than the pressure of the environment surrounding the device 100 that, when one or more holes are formed in the seal 143 by the hollow needle 120, the evacuated volume 141 acts as a suction source to draw blood from skin, through the one or more holes in the seal 143, and into contact with the sensor 140 such that the sensor 140 can detect one or more properties of the blood (e.g., a glucose concentration of the blood). In such an example, the evacuated volume 141 could additionally act as a collection chamber for blood. The evacuated volume 141 could have a pressure less than approximately 50 kilopascals. Other elements of the device 100 (e.g., the channel 145, the concave depression 123, the hole formed in the bottom of the chamber 131, the needle channel 125, or some other elements of the device 100 could act as a collection chamber for blood drawn from skin by a suction source and/or received by the device 100 by some other means.

The device 100 could additionally include a conformal layer configured to conform to the skin such that suction applied by the evacuated volume 141 (or by some other suction source of the device 100) through one or more holes in the seal 143 (or by some other means, e.g., through the needle channel 125) is applied to skin proximate the one or more holes in the seal 143. Such a conformal layer could include polyurethane, soft rubber, polymeric gel, or some other compliant material. Additionally or alternatively, such a conformal layer could include a glue (e.g., cyanoacrylate), a tape, a dry adhesive, or some other adhesive substance.

The shape, size, geometry, or other properties of the concave depression 123 could be specified to maximize an amount of blood emitted from skin in response to being pierced by the hollow needle 120. For example, the concave depression 123 could have a conical shape. The device 100 could additionally or alternatively be configured in other ways to maximize an amount of blood emitted from skin. For example, the device 100 could be configured to increase blood flow in the skin proximate the device 100 and/or proximate the concave depression 123 by, e.g., heating the skin before penetration, applying a fictive force to the skin before penetration (e.g., by rubbing the skin), applying suction to the skin before penetration, applying a vasodilating, anti-clotting, anti-coagulant, or other pharmaceutical (e.g., heparin, lidocaine) before, during, and/or after penetration of the skin, or by being configured or operated in some other way. Pharmaceuticals could be delivered as a coating on the needle 120. Additionally or alternatively, the needle 120 could be used to deliver a pharmaceutical or other substance and/or to suction blood into the device 100 via the needle channel 125.

Further, the properties of the needle 120 could be specified to maximize the amount of blood emitted from skin, maximize an amount of fluid or some other payload delivered into skin, control a depth and/or layer into which a payload is delivered into the skin, to minimize discomfort induced by penetration of the skin, or according to some other consideration. For example, the tip of the needle 120 could include a triple-bevel to minimize deflection of the skin 105 and/or to minimize induced discomfort due to piercing of the skin by the hollow needle 120. Alternatively, the needle 120 could have a chisel tip (e.g., a single bevel), could have a flat 'razor' blade end, could include a taper (e.g., could become thinner toward the end), could be round, flat, or could be configured in some other way to, e.g., maximize blood emitted from skin. The hollow needle 120 could be serrated. The diameter (or gauge) of the hollow needle 120 could be specified to maximize the amount of blood emitted from skin and/or to minimize discomfort induced by piercing of skin by the hollow needle 120. For example, the hollow needle 120 could have a gauge between approximately 21 gauge and approximately 36 gauge.

In some examples, the payload could be a fluid that includes gelling agents, and the amount, type, or other properties of the gelling agents could be specified to control an amount of the payload that is delivered into skin, a timing of delivery of the payload into the skin, or some other property of the operation of the device (e.g., by controlling a viscosity, a degree of shear thickening, an osmolarity, or some other properties of a fluid payload).

In some examples, the piston 130 could drive multiple hollow and/or solid needles into the skin. A spacing between such multiple needles, a number of the needles, the lengths and diameters of the needles, the geometry of the tips of the needles, the presence of a channel within the needles and a diameter and other properties of such a channel, or other properties of the needles could be specified to maximize the amount of blood emitted from skin pierced by the needles, to control an amount and or depth or layer to which one or more fluids or other payloads are delivered into skin by the needles, and/or to minimize discomfort induced by piercing of skin by the needles. For example, the spacing between the needles could be specified to maximize the likelihood of piercing at least one blood vessel in the skin when the piston 120 drives the needles into the skin.

Further, the distance the hollow needle 120 (or needles) pierces into skin (related, e.g., to properties of the propellant 135, chamber 131, piston 130, spring 137, hollow needle 120, and/or other elements of the device 100) could be specified to maximize the amount of blood emitted from the skin, a depth and/or layer into which the payload 155 is delivered, and/or to minimize discomfort induced by piercing of the skin by the hollow needle 120. For example, the device 100 could be configured such that the hollow needle 120 penetrates skin to a depth of approximately 2 millimeters. In some examples, the device 100 could be configured such that the hollow needle 120 penetrates skin to a depth that contains capillaries and/or other blood vessels but that does not contain many nerve endings (e.g., to a depth near the transition between the epidermis and dermis layers of the skin). Additionally or alternatively, the device 100 could be configured to drive the hollow needle 120 into the skin at a different angle than the one depicted (i.e., an angle other than approximately 90 degrees).

The propellant 135 could include a variety of chemicals and combinations of chemicals. For example, the propellant 135 could include nitrocellulose, butane, azide, or some other energetic gas-producing substance or other chemical (s). In some examples, the propellant could be formed and/or modified before use, e.g., the propellant could include oxygen and hydrogen formed from water by electrolysis. Alternatively, the propellant could include a compressed gas (e.g., $CO_2$, $N_2$, air compressed by a pump or other means, a gas generated by the device 100 by electrolysis or some other method or means) to which the piston 130 is exposed to drive the hollow needle 120 into the skin 105 and/or to deliver the payload 155 into skin though the needle channel 125. Additionally or alternatively, the piston 130 could be driven by a low pressure (e.g., a vacuum, a suction source, an evacuated volume) beneath the piston 130.

The use of the resistive element 136 to ignite the propellant 135 is intended as a non-limiting example. Other means for igniting a chemical propellant (or some other chemical or element of the device 100 according to an application) are anticipated, including but not limited to generating an electrical spark (e.g., by applying a high voltage across a spark gap or between electrodes of the device 100), illuminating the propellant (e.g., using a laser, an LED, or some other light-emitting element(s)), applying a force and/or vibration to the propellant (e.g., using a piezoelectric elements), or changing a pressure to which the propellant is exposed. Further, the illustrated configuration of the chamber 132 vent is a non-limiting example; more or fewer vents, vents located at different locations, or vents configured in some other way (e.g., through the piston 130) could be included to facilitate a piston driving a needle into skin and/or subsequently retracting the needle from the skin. In an example, one or more of the vents could be normally closed and configured to open (either permanently or temporarily) when a pressure across the vent exceeds some level (e.g., when the pressure behind the piston 130 increases above a specified pressure due to ignition of the propellant 135). Additionally or alternatively, one or more vents could be located in the chamber 131 such that gases behind the piston 130 (e.g., high-pressure gases produced by ignition of the propellant 135) are able to leave the chamber 131 through the vent only when the piston 130 is displaced downward in the chamber 131 by some specified distance.

The piston 130, chamber 131, propellant 135, spring 137, and other elements of the device 100 comprise an injector configured to drive the hollow needle 120 into skin, to deliver the payload 155 from the reservoir 150 into skin through the hollow needle 120, and subsequently to retract the needle from the skin by igniting a chemical propellant. However, the device 100 could include additional or alternative injectors configured to achieve driving of the hollow needle 120 into skin, delivery of payloads, and subsequent retraction of the hollow needle 120. In some examples, the injector could include one or more pre-loaded springs configured to be released (e.g., by a manual button, by a solenoid or other electromechanical actuator). The injector could include one or more magnets and/or cams configured to translate a force between the one or more magnets and other elements of the device 100 to produce driving and/or retracting force(s) that could be applied to the hollow needle 120 and/or elements of the reservoir 150. In some examples, the injector could include one or more motors or other electromechanical actuator configured to apply driving and/or retracting force(s) directly to the hollow needle 120 and/or reservoir 150 (e.g., through a rack-and-pinion mechanism, using a cam, by applying magnetic forces using a solenoid) and/or by charging up a spring (e.g., a rotary spring) that could apply such force(s). In some examples, the hollow needle 120 could be applied against the skin with a constant force that is less than a force necessary to pierce the skin, and a vibrator (e.g., a vibrating motor, a piezoelectric or otherwise configured ultrasonic transducer) could vibrate the hollow needle 120 such that the hollow needle 120 pierces the skin. Other injectors or other means and methods for driving the hollow needle 120 into the skin, delivering the payload 150 through the needle channel 125 into the skin, and subsequently retracting the needle are anticipated.

Suction applied to the seal 143 and/or to some other element(s) of the device 100 could be applied by a variety of means or methods. As illustrated in FIGS. 1A and B, suction can be provided by an evacuated volume 141 that has a pressure that is lower than the pressure of the atmosphere surrounding the device 100. Additionally or alternatively, suction could be provided by a pump, a chemical process that causes a decrease in pressure (e.g., by causing a decrease in temperature, by consuming nitrogen, oxygen, or some other gas from an enclosed volume (e.g., 141) and/or by changing a phase of such gases), a spring-loaded or otherwise actuated, enclosed volume that can be actuated to increase in size (thus producing suction), or by some other means of producing suction. In some examples, blood emitted from skin (e.g., due to penetration of the skin with a needle as described herein) could be drawn into the device 100, applied to a sensor (e.g., 140), stored, or otherwise manipulated according to an application without using a source of suction, e.g., by using hydrophobic and/or hydrophilic coatings and/or capillary forces to control the location and/or movement of blood within and/or relative to the device 100, by locating a sensor, blood storage element, or other element(s) of the device 100 proximate to the location at which the device 100 pierces the skin with the hollow needle 120, or by configuring the device 100 in some other way. In some examples, e.g., when the hollow needle 120 pierces a vein or other larger vasculature, blood pressure or other forces within or beneath skin may cause a sufficient amount of blood to be emitted from the skin.

When suction is provided by a suction source that comprises an evacuated volume (e.g., 141), a pressure within the evacuated volume could be specified to provide sufficient suction, for example, the pressure within the evacuated volume could be less than approximately 50 kilopascals. Further, the device 100 could be constructed such that the evacuated volume has a pressure less than some maximum value (e.g., 50 kilopascals) for some specified minimum period of time such that the evacuated volume could be used as a suction source to draw blood into the device 100 at a specified future point in time. This could include the device 100 including high-quality seals and adhesives between elements of the device 100 that comprise and/or form the evacuated volume. In some examples, surfaces of elements (e.g., the housing 110, the seal 143, the circuit board 115) of the device 100 that are joined to form the evacuated volume could have highly smooth surfaces. In some examples, the device 100 could be configured and/or assembled such that the pressure within the evacuated volume remains below a specified maximum pressure for 48 hours, a week, or some other specified period of time to permit the use of the evacuated volume to provide suction to draw blood into the device 100 at a specified future point in time that is less than the specified period of time. In some examples, this could include storing the device 100 in an evacuated volume of a package (e.g., within an evacuated and sealed blister of packaging material) and removing the device 100 from the evacuated volume of the package before mounting the device 100 to skin.

The seal 143 could be composed of a variety of materials to allow suction to be applied to and contained by the seal 143 until the seal is pierced by the hollow needle 120. Further, the seal 143 could be composed of materials that are capable of being vacuum-formed into a specified shape (e.g., a shape that can be mounted to the housing 110 and that includes one or more concave depressions, e.g., 123). For example, the seal 143 could be composed of polycarbonate.

The sensor 140 could be configured to detect a variety of properties of blood drawn into the device 100. For example, the sensor 140 could be configured to detect the presence, concentration, or other properties of an analyte (e.g., glucose, small molecules, cells, cell counts, hormones, cholesterol, testosterone, thyroid hormones, vitamins, minerals, electrolytes, cortisol, creatinine, luteinizing hormone, follicle stimulating hormone) in the blood. In some examples, the sensor 140 could be configured to detect a clotting rate, viscosity, osmolarity, or other property of the blood. The sensor 140 could be configured to detect the property of the blood through direct contact between the blood and one or more elements of the sensor 140. For example, the sensor 140 could be an electrochemical sensor configured to amperometrically, potentiometrically, or otherwise electrochemically detect one or more properties of the blood when the blood comes into contact with one or more electrodes of the electrochemical sensor (e.g., when the blood comes into contact with a working electrode of the sensor 140 that is selectively sensitive to an analyte of interest in the blood and further comes into contact with a reference electrode of the sensor 140). In another example, the sensor 140 could be configured to detect a property of the blood when the blood comes into contact with an analyte-sensitive chemical (e.g., a fluorophore, a chromophore) that has one or more optical properties (e.g., a color, a fluorescence intensity, a fluorescence lifetime) that are related to the analyte in the blood, and the sensor 140 could detect the analyte in the blood by optically interrogating (e.g., illuminating and/or detecting light emitted from) the analyte-sensitive chemical. Additionally or alternatively, the sensor 140 could be configured to detect one or more properties of the blood without being in direct contact with the blood, e.g., by detecting a color of the blood, a property of motion of the blood, or some other property.

In some examples, the sensor 140 (or some other components of the device) could be configured to interact with micro- or nano-particles delivered into the skin and/or to interact with electronics (e.g., a microelectronic biosensor) delivered into the skin by the payload-delivering device 100. For example, the payload 155 could include a plurality of microparticles and/or nanoparticles configured to have a property that can be interrogated and/or detected by the sensor 140 and that is related to one or more properties of the skin. For example, the payload could comprise a plurality of particles that are sensitive to an analyte in the skin and/or in the body (e.g., a protein, a cancer cell). Further, the particles could have an optical, electrical, magnetic, electromagnetic, or other property that is related to a property of the analyte (e.g., a concentration of the analyte, a state of the analyte, binding of the analyte to one or more of the particles) such that the particles emit electromagnetic energy related to (e.g., having an amplitude, frequency, polarization, phase, timing, wavelength or other property related to) the property of the analyte in response to receiving interrogating electromagnetic energy (e.g., in response to the sensor 140 or some other device emitting radio frequency energy toward the particles in the skin). In some examples, the particles emitting electromagnetic energy could include the particles reflecting, absorbing, fluorescently or otherwise absorbing and re-emitting, or otherwise interacting with the interrogating electromagnetic energy. Additionally or alternatively, some system other than the sensor 140 and/or device 100 could be configured and operated to detect one or more properties of the skin by interacting with such microparticles and/or nanoparticles delivered into the skin by the device 100.

In another example, the payload could include one or more electronic devices configured to perform some function within and/or beneath the skin. For example, the payload could be an electronic biosensor that includes one or more sensors configured to detect a property of skin and/or of some other tissue to which the sensor(s) is exposed (e.g., to detect a concentration of an analyte, to detect an electrical field, to detect a temperature, to detect a pH). The electronic biosensor could further include microfabricated electronics configured to operate the sensor(s), to receive energy wirelessly to power the electronic biosensor (e.g., to receive RF energy emitted by the sensor 140 and/or by some other component(s) of the device 100), to receive energy electrochemically from the skin to power the electronic biosensor, to record information about the skin detected using the sensor(s), to transmit information about the skin detected using the sensor(s) to the sensor 140 and/or to some other component(s) of the device 100 (e.g., by reflecting electromagnetic energy emitted toward the electronic biosensor as backscatter radiation), or to perform some other operations of an the electronic biosensor according to an application. Additionally or alternatively, some system other than the sensor 140 and/or device 100 could be configured and operated to operate the electronic biosensor (e.g., by emitting electromagnetic radiation toward and/or receiving electromagnetic radiation from the electronic biosensor). A device as described herein could be configured to store blood emitted and/or drawn from skin (e.g., for some later analysis). Such a blood storage element could include a capillary tube, an ampoule, a basin, a pit, or some other geometry configured to contain blood. Further, a blood storage element could be configured to preserve, chemically modify, prevent clotting or coagulation of, or otherwise manipulate the stored blood. For example, the blood storage element could contain heparin to prevent clotting and/or coagulation of drawn, stored blood. Alternatively, the blood storage element could be configured to allow the blood to dry, according to an application. In some examples, the blood storage element could include an absorptive material, e.g., a piece of fabric configured to absorb blood or other fluids.

Stored blood could be presented to a sensor or other element(s) of a sensing device (e.g., a desktop or other device separate from a blood-accessing device as described herein, e.g., 100) configured to detect one or more properties of the stored blood. For example, a blood accessing device could be configured to be mounted to such a sensing device and to provide the stored blood to the sensing device. This could include the sensing device detecting one or more properties of the stored blood while it remains in the blood-accessing device (e.g., by optically detecting a property of the stored blood by illuminating and/or receiving light from the stored blood through a window, an optical fiber, or other optically transparent elements of the blood-accessing device). Additionally or alternatively, the blood-accessing device providing the stored blood to a sensing device could include the stored blood being removed from a blood storage element or other components of the blood-accessing device.

A payload-delivering and/or blood-accessing device or system as described herein (e.g., 100) could include multiple sensors, blood-storage elements, needles, injectors, seals, and/or other elements. For example, a device could include multiple sections that each include a respective hollow needle, injector, reservoir, suction source, and/or other elements. Each section could be configured to drive its respective hollow needle into skin, to subsequently deliver a payload from a respective reservoir into the skin through the needle, to retract the needle from the skin, and to receive blood emitted from the skin in response to being penetrated by the needle. Each section could include one or more sensors, one or more blood storage elements, and/or additional components configured to receive, transmit, measure, modify, or otherwise interact with blood received from the skin. The sections of a device could be similarly configured (e.g., could include similar sensors, be configured to draw similar amounts of blood from skin in a similar manner, be configured to deliver a similar fluid, drug, or other payload) or could be differently configured (e.g., different sensors, differently configured injectors, differently configured needles, different delivered fluids/drugs/payloads). The sections of a device could be operated to access blood from skin and/or deliver a payload into skin at respective different points in time, e.g., at a number of points in time while a wearer of the device is asleep, at a number of points in time during a week, in response to a command received from a user and/or from a remote system in communication (e.g., wireless communication via Bluetooth, ZigBee, WiFi, or some other wireless communications protocol), in response to a detected command (e.g., a button press) and/or behavior (e.g., performance of an exerting athletic activity, detected using, e.g., an accelerometer of the device 100) of a wearer, based on a detected physiological state of the wearer (e.g., a heart rate or blood pressure detected by sensor(s) of the device 100), or according to some other scheme.

Further, a device could include more or fewer sections, organized similarly or differently (e.g., in a row, rather than circularly as illustrated) than those embodiments illustrated herein. For example, a blood-accessing device could include a single section (e.g., device 100). In examples wherein the injector and/or suction source are single-use (e.g., wherein the injector ignites a limited supply of a propellant and/or wherein suction is provided by a single evacuated volume) and the device includes a single such section, the blood-accessing and/or payload-delivering device could be configured for a single use. In some examples, such a single and/or limited-use (e.g., a single use, as illustrated in FIG. 1A) device could be configured to be a removable and/or replaceable element of some other device. For example, the blood-accessing and payload-delivering device 100 could be configured to be removably mounted on or within a body-mountable device (e.g., a wrist-mountable device) that includes a controller, a user interface, a battery, a communications interface, or some other elements. Such a body-mountable device could be configured to operate the limited-use device to access a number of samples of blood from skin and/or to deliver a number of amounts of a fluid or other non-discrete payload into skin (e.g., at respective specified points in time). Once the body-mountable device has operated all of the limited-use sections of the device, the device could be removed from the body-mountable device and replaced. In some examples, the removed device could be configured to store blood, and blood stored in the removed blood-accessing device could be presented to a sensing device for analysis (e.g., the removed device could be sent via post to a sensing device at a laboratory that is remote from a user of the body-mountable device).

FIGS. 2A-D illustrate the operation of a device 200 to deliver a payload into skin 205 and to access blood from the skin 205. The device 200 includes a housing 210 into which is formed a chamber 231. The chamber contains a hollow needle 220 configured to penetrate the skin 205. A piston 230 is coupled to the needle 220 and configured to slidably move within the chamber 231. A reservoir 250 containing a payload 255 is formed in the piston 230 and coupled to a channel of the hollow needle 220. The chamber 231 additionally contains a propellant 235 configured to slidably move the piston 230 within the chamber 231 to drive the hollow needle 220 into skin 205 and to apply a force to reduce a volume of the reservoir 250 such that the payload 255 is delivered from the reservoir 250 through the hollow needle 220 and into the skin 205. The chamber additionally contains a spring 237 configured to retract the hollow needle 220 from the skin and a resistive element 236 configured to ignite the propellant 235.

A hole is formed in the bottom of the chamber 231 through the housing 210 such that the hollow needle 220 can be driven into skin 205 proximate the bottom of the housing 210. A chamber vent 232 is formed in the housing 210 to allow gases produced by the ignition of the propellant 235 to be vented out of the device such that the spring 237 can retract the hollow needle 220 subsequent to the ignited propellant 235 causing the piston 230 to drive the hollow needle 220 into the skin 205. A sensor 140 is located proximate the location on the skin 205 that could be pierced by the hollow needle 120.

Figure 2A:
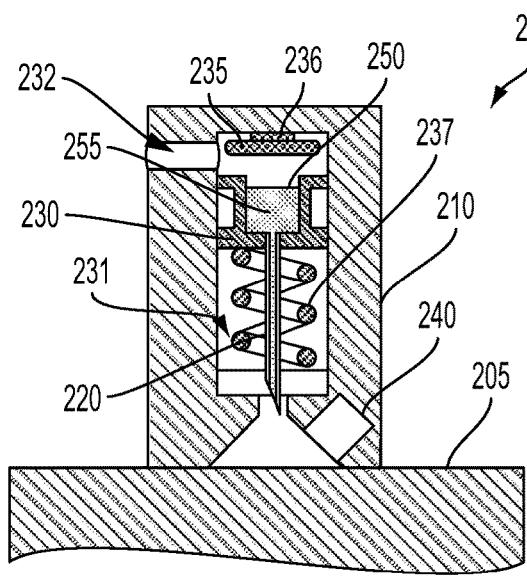
FIG. 2A is a cross-sectional view of an example device mounted to a skin surface.

FIG. 2A shows the device 200 having been mounted to the skin 205; this could include the device 200 being a handheld device designed to be manually or otherwise maintained in contact with the skin 205. Alternatively, the device 200 could be adhered to the skin 205 using an adhesive or mount (e.g., a mount configured to encircle a wrist of a person such that the device 200 is maintained in contact with skin of the wrist). In another example, the device 200 could be a desktop or other relatively immobile device and a body part comprising the skin 205 could be positioned proximate the device 200 as illustrated.

Figure 2B:
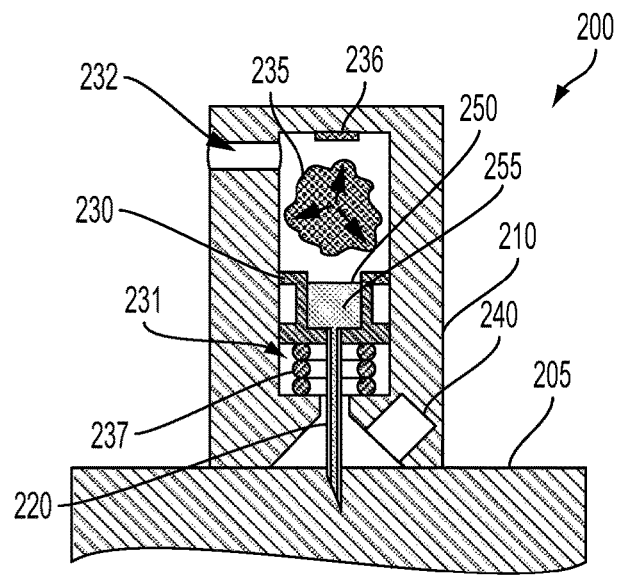
FIG. 2B is a cross-sectional view of the example device of FIG. 2A when a needle of the example device is piercing the skin.

FIG. 2B shows the propellant 235 expanding to slidably move the piston 230 downward, compressing the spring 237 and driving the hollow needle 220 into the skin 205. Properties of the spring 237 (e.g., a spring constant, a degree of initial loading), piston 230 (e.g., a mass, a coefficient of friction with the sides of the chamber 231, a diameter and number of piston vents 232), hollow needle 220 (e.g., a diameter, a tip geometry, the presence of a fluoropolymer coating or other anti-friction coating), chamber 231 (e.g., a geometry, a volume of the region above the piston), propellant 235 (e.g., an amount of the propellant, a mix of chemicals comprising the propellant), or other elements of the device 200 could be specified to maximize the speed with which the needle 220 is driven into the skin 205 to, e.g., reduce discomfort induced in a user by operation of the device 200 to penetrate the skin 205.

Figure 2C:
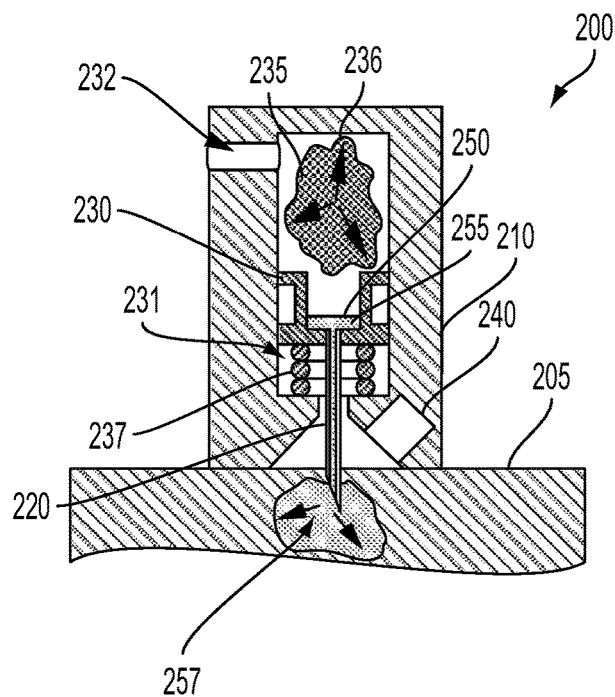
FIG. 2C is a cross-sectional view of the example device of FIG. 2B when the fluid contained in the example device is being delivered into the skin.

FIG. 2C shows the propellant 235 further expanding to apply a force to reduce a volume of the reservoir 250 such that the payload 255 is delivered into the skin 205 through the hollow needle 220 (as delivered payload 257; note that the payload, in this example, is a fluid, but that other payloads, including gels, polymers, solid materials, polymers, micro- and nano-particles, microelectronic components, or other materials or combinations of materials are anticipated). Properties of the reservoir 250 (e.g., a spring constant and/or compliance of an elastic membrane of the reservoir 250 separating the payload 255 from the expanding propellant 235, a shear strength of a collapsible or partially collapsible element of the reservoir 250), hollow needle 220 (e.g., a diameter, a tip geometry, the presence of a fluoropolymer coating or other anti-friction coating), propellant 235 (e.g., an amount of the propellant, a mix of chemicals comprising the propellant, a pressure profile of the ignited propellant 235 subsequent to ignition), payload 255 (a viscosity, density, degree of shear thickening, osmolarity, or other properties of a fluid of the payload 255 controlled or affected by the addition of gelling agents or other substances; a geometry, size, and/or rigidity of a microelectronic device or of some other solid, gel, or semi-solid objects of the payload 255; some other properties of the payload 255), or other elements of the device 200 could be specified to control an amount, a rate of delivery, a timing of delivery (e.g., a timing relative to driving the hollow needle 120 into the skin 205 and/or relative to retraction of the hollow needle 220 form the skin 205), a depth or delivery, or other properties of the delivery of the payload 255 into the skin 205, or to control some other properties of operation of the device 200.

Figure 2D:
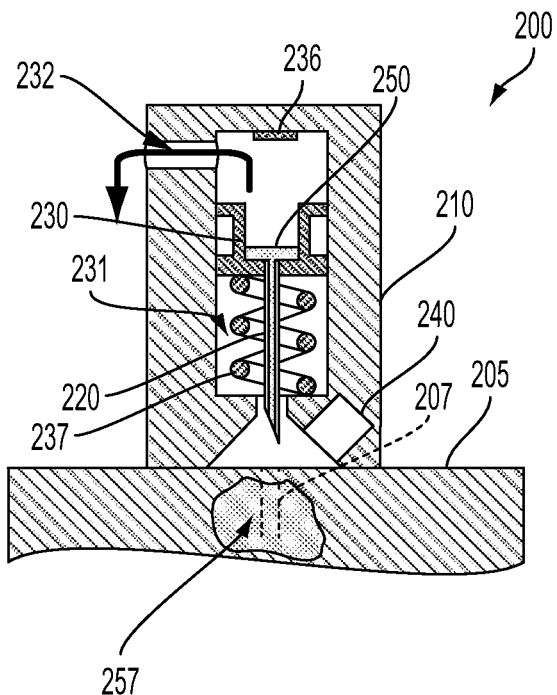
FIG. 2D is a cross-sectional view of the example device of FIG. 2C when the needle of the example device has retracted from the skin.

FIG. 2D shows the piston 230 and hollow needle 220 retracted from the skin 205 partially due to venting of propellant gases through the chamber vent 232 (indicated by the arrow) and the force generated by the spring 237 due to compression of the spring 237 by the movement of the piston 230 downward when driving the hollow needle 220 into the skin 205 (shown in FIGS. 2B and 2C). FIG. 2D additionally shows a puncture 207 formed in the skin 205 by the piston 230 driving the hollow needle 220 into the skin 205. Properties of the spring 237, piston 230, hollow needle 220, chamber 231, propellant 235, or other elements of the device 200 could be specified to maximize the speed with which the needle 220 is retracted from the skin 205 and/or minimize the duration during which the needle 220 pierces the skin 205 to, e.g., reduce discomfort induced in a user by operation of the device to penetrate the skin 205.

Figure 2E:
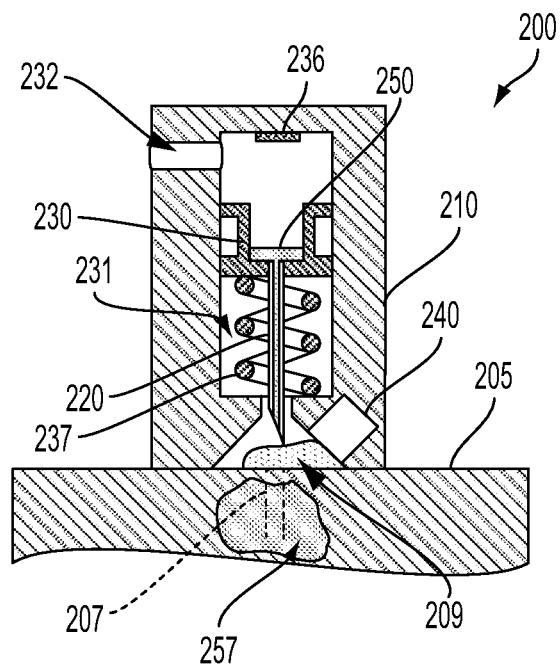
FIG. 2E is a cross-sectional view of the example device of FIG. 2D when a sensor of the example device has been exposed to blood from the skin.

FIG. 2E shows blood 209 emitted from the skin 205 (e.g., from the puncture 207 formed in the skin 205). The sensor 240 is exposed to the blood 209. This could include suction generated by the device 200 drawing the blood 209 form the puncture 207 to the sensor 240. Additionally or alternatively, the blood 209 could be directed to the sensor 240 by hydrophobic and/or hydrophilic coatings on one or more surfaces of elements of the device 200 (e.g., of the housing 210). For example, a path from the puncture 207 to the sensor 240 could be coated with a hydrophilic substance; other surfaces of the device 200 that could come into contact with the blood 209 could be coated with a hydrophobic substance. Additionally or alternatively, elements of the device 200 (e.g., a capillary tube or channel formed, e.g., in the housing 210) could be sized to direct the blood 209 using capillary action. Elements of the device 100 (e.g., the sensor 140, a blood collection element) could include a coating of heparin or some other pharmaceutical to reduce coagulation and/or clotting of the blood 209 on or in the device (e.g., to increase the duration and/or amount of blood 209 flowing into the device 200 and/or to the sensor 240).

Note that a device could include more components than those illustrated in FIGS. 1A, 1B, and 2A-E and/or could lack some elements and/or features illustrated in FIGS. 1A, 1B, and 2A-E. For example, a device could lack the spring 137/237, could lack the vent 132/232, and/or could be otherwise configured not to automatically retract the hollow needle 120/220 subsequent to driving the hollow needle 120/220 into skin. Further, a device could lack a suction source (e.g., 141) and/or sensor (e.g., 140/240) and/or include a blood collection element.

In some examples, a device could be configured to draw, receive, or otherwise collect blood emitted from skin pierced by the hollow needle 120/220 through the needle channel 125. For example, the reservoir 150/250 could include a spring, an elastic member, an elastic membrane, or some other mechanically resilient element configured to counter force applied to reduce a volume of the reservoir 150 by the propellant 135 and/or by some other element of an injector or some other system of the device 100. Such a counter force could act to increase a volume of the reservoir to provide suction through the hollow needle such the blood or other fluids from the skin are drawn into the device through the hollow needle.

Such a mechanically resilient element could be provided according to additional or alternative applications, e.g., to control a timing or some other property of the delivery of a payload into skin. As an example, FIG. 3A shows a device 300 including a hollow needle 320 coupled to a piston 330 disposed in a chamber 331 formed in the device 300. The piston 330 includes a reservoir 350 containing a fluid payload (e.g., a drug, an inoculant). The reservoir 350 is coupled to the hollow needle 320 and contains a mechanically resilient element (i.e., a spring 337) configured to apply a force that is counter to a force applied by the propellant 335 that is, in FIG. 3A, expanding to drive the hollow needle 320 into skin by applying a force on the piston 330.

FIG. 3B shows the device 300 when the propellant 335 has exerted sufficient force to drive the hollow needle 320 into the skin. Further, the force exerted by the propellant (e.g., related to the increasing pressure of the propellant) is sufficient to overcome the force applied by the spring 337 such that a volume of the reservoir 350 is reduced, delivering the fluid payload from the reservoir 350 into the skin through the hollow needle 320. Additionally or alternatively, such a mechanically resilient element (e.g., a spring 337, an elastic membrane) could be provided to control a timing of delivery of the fluid payload from the reservoir 350 through the hollow needle 320. For example, the spring 337 could be provided in the reservoir 550 to increase a force applied by the propellant 135 that is necessary to reduce the volume of the reservoir 150 such that the timing of delivery of the fluid payload 155 is delayed.

A device could be configured in a variety of different ways to drive a hollow needle into skin and to deliver a payload into the skin through the hollow needle. In some examples, this could include accelerating the hollow needle and/or some other elements of the device (e.g., a piston, a reservoir containing the payload and coupled to the hollow needle) toward the skin and then arresting the motion of the hollow needle in a manner that results in the payload being delivered through the hollow needle, e.g., by converting the motion of the hollow needle and/or other elements of the device into a force applied to reduce a volume of the reservoir containing the payload. As an example, FIG. 4A shows a device 400 including a hollow needle 420 coupled to a piston 430 disposed in a chamber formed in the device 400. The piston 430 includes a reservoir 450 containing a fluid payload (e.g., a drug, an inoculant). The reservoir 450 is coupled to the hollow needle 420. The propellant 435 is, in FIG. 4A, expanding to drive the hollow needle 420 into skin by applying a force on the piston 430.

FIG. 4B shows the device 400 when the propellant 435 has exerted sufficient force to drive the hollow needle 420 into the skin. A stop 417 formed in the device 400 has arrested the motion of the hollow needle 420, piston 430, and reservoir 450; further, the stop 417 arresting the hollow needle 420, piston 430, and reservoir 450 causes the stop 417 to apply a force to reduce a volume of the reservoir 450 such that fluid payload is delivered from the reservoir 450 into the skin through the hollow needle 420. Additionally or alternatively, force applied by the expanding propellant 435 could exert a force, through the stop 417, to reduce a volume of the reservoir 450 such that fluid payload is delivered from the reservoir 450 into the skin through the hollow needle 420.

Figure 5A:
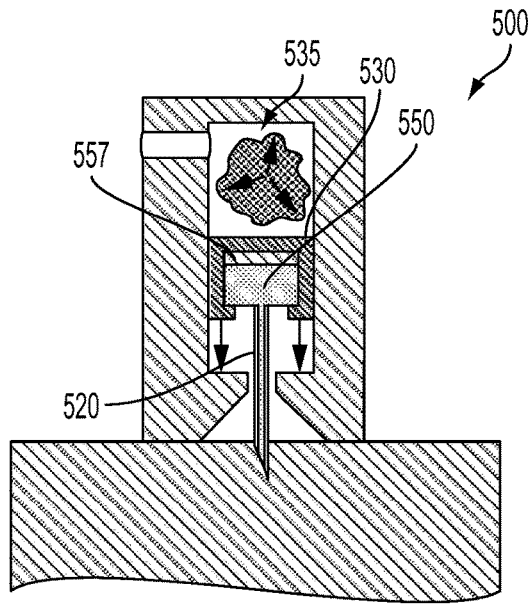
FIG. 5A is a cross-sectional view of an example device mounted to a skin surface when a needle of the example device is piercing the skin.

In another example, FIG. 5A shows a device 500 including a hollow needle 520 coupled to a piston 530 disposed in a chamber formed in the device 500. The piston 530 includes a reservoir 550 containing a fluid payload (e.g., a drug, an inoculant). The reservoir 550 is coupled to the hollow needle 520. The reservoir includes a driving mass 557 configured to slidably move within the piston 530. The propellant 535 is, in FIG. 5A, expanding to drive the hollow needle 520 into skin by applying a force on the piston 530 to accelerate the hollow needle 520, the piston 530, the reservoir 550, and the driving mass 557 toward the skin.

Figure 5B:
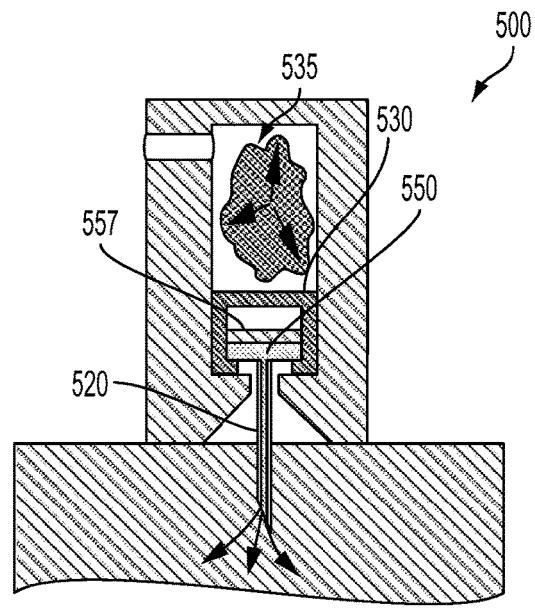
FIG. 5B is a cross-sectional view of the example device of FIG. 5A when the fluid contained in the example device is being delivered into the skin.

FIG. 5B shows the device 500 when the propellant 535 has exerted sufficient force to drive the hollow needle 520 into the skin. A stop formed in the device 500 has arrested the motion of the hollow needle 520, piston 530, and reservoir 550 toward the skin. The driving mass 557 has a sufficient mass to continue moving toward the skin subsequent to the stop arresting the motion of the hollow needle 520, piston 530, and reservoir 550. The continued motion of the driving mass 557 causes the driving mass 557 to apply a force to reduce a volume of the reservoir 550 such that fluid payload is delivered from the reservoir 550 into the skin through the hollow needle 520.

Figure 6A:
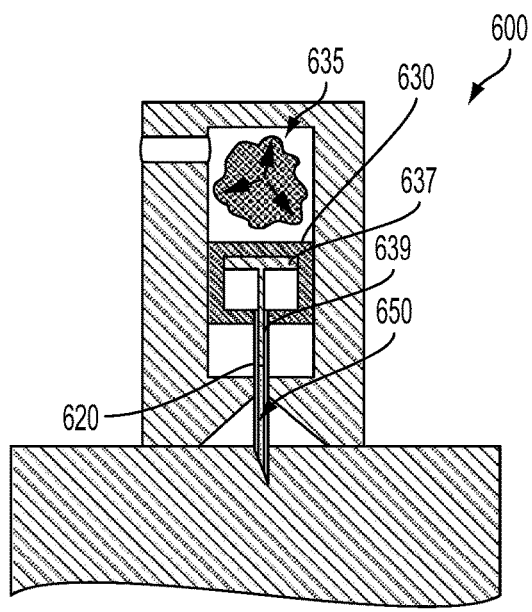
FIG. 6A is a cross-sectional view of an example device mounted to a skin surface when a needle of the example device is piercing the skin.

A driving mass of a device (e.g., 557) that is configured to continue moving subsequent to the arrest of the motion of a hollow needle (e.g., 520) and/or other elements (e.g., 530, 550) of a device by skin, by a stop of the device, and/or by some other element(s) of the device could be coupled to a payload and/or to a reservoir containing such a payload in a variety of ways to allow the continued motion of the driving mass to deliver the payload into the skin through the hollow needle. As an example, FIG. 6A shows a device 600 including a hollow needle 620 coupled to a piston 630 disposed in a chamber formed in the device 600. The channel of the hollow needle 620 comprises a reservoir 650 containing a fluid payload (e.g., a drug, an inoculant). A driving mass 637 is disposed in the piston 630 and configured to slidably move within the piston 630. An inner needle 639 is disposed at least partially within the channel of the hollow needle 620 and is coupled to the driving mass 637. The propellant 635 is, in FIG. 6A, expanding to drive the hollow needle 620 into skin by applying a force on the piston 630 to accelerate the hollow needle 620, the piston 630, the inner needle 639, and the driving mass 637 toward the skin.

Figure 6B:
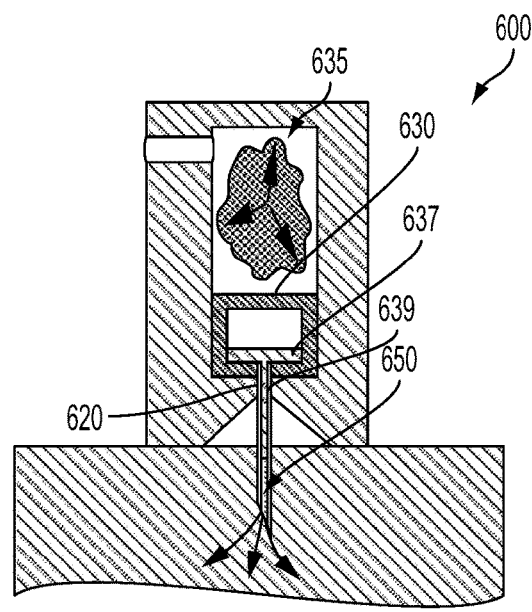
FIG. 6B is a cross-sectional view of the example device of FIG. 6A when the fluid contained in the example device is being delivered into the skin.

FIG. 6B shows the device 600 when the propellant 635 has exerted sufficient force to drive the hollow needle 620 into the skin. A stop formed in the device 600 has arrested the motion of the hollow needle 620 and piston 630 toward the skin. The driving mass 637 and inner needle 639 have a sufficient mass to continue moving toward the skin subsequent to the stop arresting the motion of the hollow needle 620 and piston 630. The continued motion of the driving mass 637 and inner needle 639 causes the driving mass 637 and inner needle 639 to apply a force to reduce a volume of the reservoir 650 such that the fluid payload is delivered from the reservoir 650 into the skin.

Figure 7A:
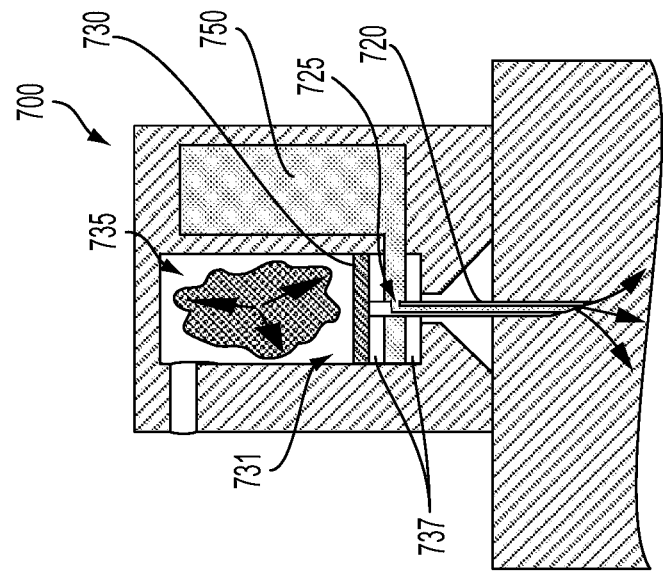
FIG. 7A is a cross-sectional view of an example device mounted to a skin surface when a needle of the example device is piercing the skin.

In some examples, the injector could act to couple the channel of the hollow needle with a fluid-containing reservoir (e.g., a reservoir containing a payload fluid under pressure) by opening a valve, moving the needle and/or reservoir relative to each other such that they are coupled, by breaching a seal, or by some other coupling means such that the payload is able to be delivered through the hollow needle subsequent to driving the hollow needle into the skin. In an example, FIG. 7A shows a device 700 including a hollow needle 720 coupled to a piston 730 disposed in a chamber formed in the device 700. The hollow needle 720 passes through two seals 737 and includes a side-channel 725 connected to the channel in the hollow needle 720. The device 700 includes a reservoir 750 containing a fluid payload (e.g., a drug, an inoculant). The reservoir 550 extends into the space between the two seals 737. The propellant 735 is, in FIG. 7A, expanding to drive the hollow needle 720 into skin by applying a force on the piston 730 to drive the hollow needle 720 into the skin.

Figure 7B:
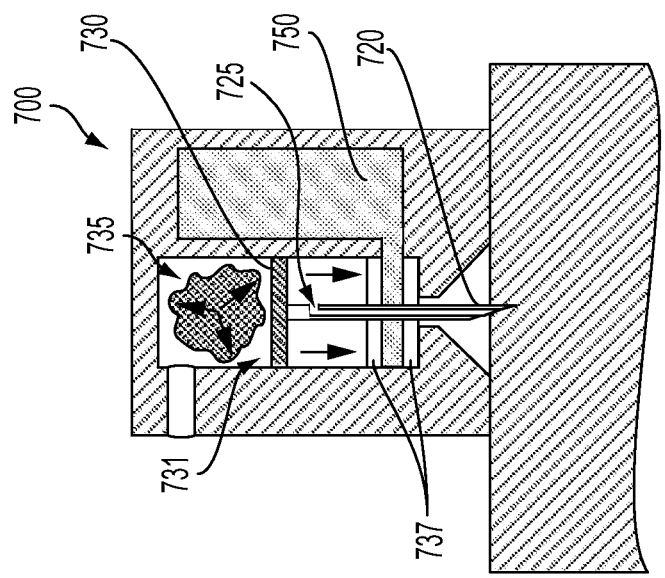
FIG. 7B is a cross-sectional view of the example device of FIG. 7A when the fluid contained in the example device is being delivered into the skin.

FIG. 7B shows the device 700 when the propellant 735 has exerted sufficient force to drive the hollow needle 720 into the skin. The motion of the hollow needle 720 in the chamber has caused the side channel 725 to enter the space between the seals 737. As a result, the reservoir 750 is coupled to the channel of the hollow needle 720, allowing the payload to be delivered into the skin through the channel of the hollow needle 720. In some examples, this could include the reservoir 750 being pressurized (i.e., the payload and/or other fluids (e.g., air pocket(s)) within the reservoir 750 could be at a higher pressure than the environment surrounding the device 700/in the skin). The reservoir could be pressurized during manufacture (e.g., the seals and other elements of the device 700 could be configured to maintain a high pressure within the reservoir 750 from the time of manufacture of the device 700 until use). In some examples, the reservoir 750 could be pressurized prior to driving the hollow needle 720 into the skin using a pump or by some other means. For example, a vent, membrane, or other elements could be included to transmit some of the pressure produced by the ignited propellant 735 into the reservoir 750 to pressurize the reservoir 750. Note that the configurations and operations of devices as described herein are meant as non-limiting examples of operation of devices configured to puncture skin, to deliver fluids and/or other payloads into the skin, and/or to receive blood emitted from the skin in response to being punctured. Such devices could include a variety of means for penetrating or piercing skin, for driving such penetrating means into skin, for delivering such payloads into the skin, for subsequently retracting such penetrating means from the skin, for drawing, wicking, suctioning, or otherwise receiving blood responsively emitted from the skin, for storing the received blood, for sensing one or more properties of the received blood, for moving, directing, preserving, or otherwise interacting with the received blood, or for performing some additional or alternative operations of functions according to an application.

III. EXAMPLE DEVICES

Payload-delivering and/or blood-accessing devices as described herein can be configured to be mounted to an external body surface of a wearer and to enable a variety of applications and functions including deliver of fluids, vaccines, inoculants, and/or other payloads into the body of a person, accessing blood of the person (e.g., drawing, extracting, or otherwise receiving blood), storing such accessed blood, detecting one or more properties of such accessed blood, detecting some other properties of the body of the person (e.g., a pulse rate), or performing some other functions. Such devices could enable a variety of applications, including measuring homological properties or other physiological information about a person, indicating such measured information or other information to the person (e.g., using a vibrator, a screen, a beeper), recording such information, indicating such information to a remote system (e.g., a server in a physician's office), or other functions.

In some examples, a payload-delivering and/or blood-accessing device is provided as a handheld device, as shown in FIGS. 8A and 8B. The handheld device 800 may be mounted to the skin of a living subject by positioning the device 800 (e.g., by positioning a contact surface 815 of the device 800) proximate the skin. The handheld device 800 can be configured to deliver a payload into skin of a living subject, to access blood of a living subject, and to store, detect a property of, or otherwise interact with such accessed blood. In order to deliver payloads to and/or access blood from within and/or beneath skin of the living subject, the handheld device may be positioned on a portion of the body where subsurface vasculature or other targets or elements of the living subject are easily accessed (e.g., punctured), the qualification of which will depend on the type of system used. A housing 810 is provided to permit manual positioning of the device 800 on the living subject. A contact surface 815 of the device 800 is intended to be mounted facing to the external body surface. The device 800 may include sensors (e.g., 830) disposed on the contact surface 815 and/or within the housing 810 for detecting one or more physiological properties of the wearer (e.g., a pulse, a blood oxygenation, a galvanic skin response). The contact surface 815 additionally includes a concave depression 820. The concave depression 820 corresponds to a payload delivering and/or blood-accessing section of the device 800 that can be operated to drive a hollow needle, through the concave depression (e.g., through a seal of the device and/or through a channel of the device configured to allow the passage of the hollow needle), into skin of a wearer and to deliver a payload into the skin of the wearer through the hollow needle. The device 800 could additionally be operated to subsequently retract the hollow needle from the skin. Further, the payload delivering and/or blood-accessing section could be configured to receive blood responsively emitted from the skin (e.g., by wicking, capillary action, application of suction, or some other means) and to store, detect a property of, or otherwise interact with the received blood (e.g., to detect a property of emitted blood that comes into contact with the sensor 830).

The handheld device 800 may also include a display 850 where a visual indication of information about the operation of the device 800 may be displayed. The display 850 may further be configured to provide an indication of a measured hemodynamic property of blood accessed from the body of the wearer using the device (e.g., to provide an indication of a blood glucose level of the wearer's blood). Further, the handheld device 800 may include one or more buttons 840 for accepting inputs from the wearer. For example, the button 840 may be configured to accept inputs for controlling aspects of the device 800, such as initiating a measurement period (e.g., causing the device 800 to access blood of the wearer by driving a needle into skin or according to some other method), and/or initiating a delivery of a payload (e.g., a fluid containing insulin) into skin of the wearer.

Figure 9A:
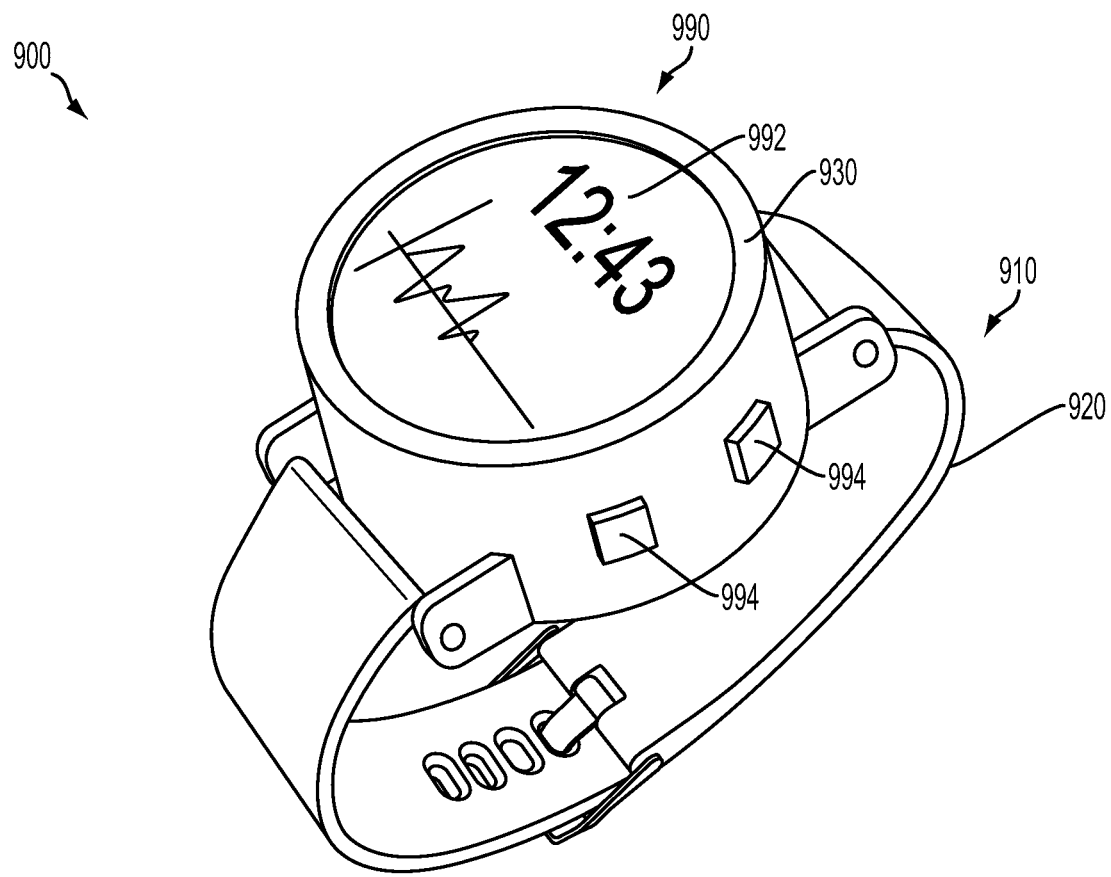
FIG. 9A is a perspective top view of an example wearable body-mountable device.
Figure 9B:
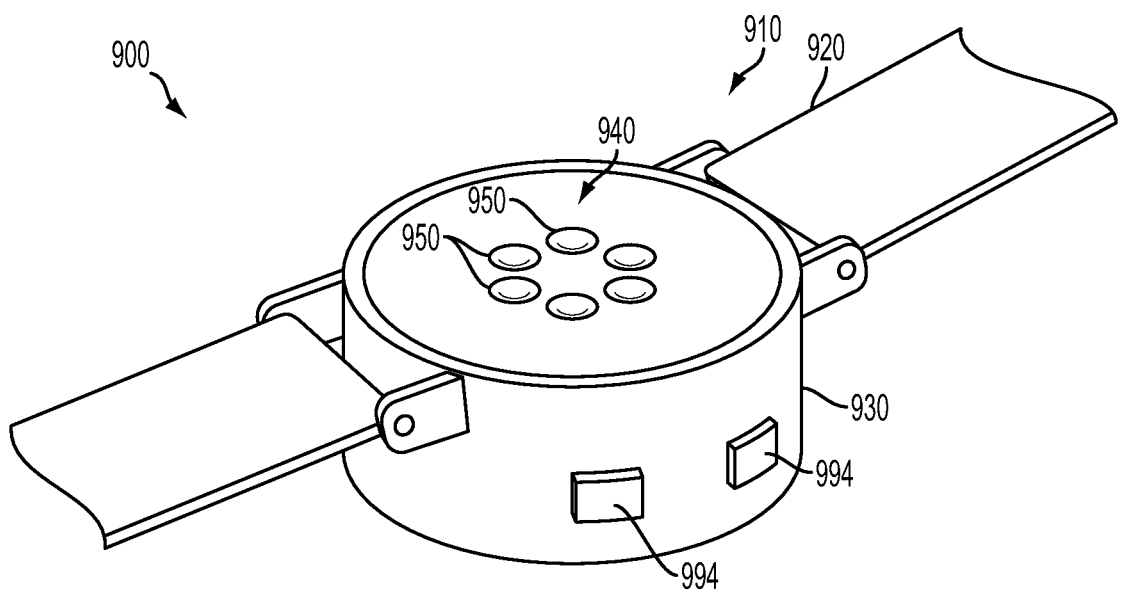
FIG. 9B is a perspective bottom view of the example wearable body-mountable device shown in FIG. 9A.

In some examples, a wearable device is provided as a wrist-mounted device, as shown in FIGS. 9A and 9B. The wrist-mounted device 900 may be mounted to the wrist of a living subject with a wristband or cuff, similar to a watch or bracelet. The wearable device 900 can be configured to deliver a payload into skin of a wearer, to access blood of a wearer, and to store, detect a property of, or otherwise interact with such accessed blood. The term "wearable device," as used in this disclosure, refers to any device that is capable of being worn at, on or in proximity to a body surface, such as a wrist, ankle, waist, chest, or other body part. In order to deliver payloads into and/or access blood from within and/or beneath skin of the body, the wearable device may be positioned on a portion of the body where subsurface vasculature or other targets or elements of the body of the wearer are easily accessed (e.g., punctured), the qualification of which will depend on the type of system used. A mount 910, such as a belt, wristband, ankle band, etc. can be provided to mount the device at, on or in proximity to the body surface. The mount 910 may prevent the wearable device from moving relative to the body to allow for blood to be drawn from a puncture produced in the skin by the device 900 (e.g., by a driven and subsequently retracted needle of the device) or according to some other application or consideration. In one example, shown in FIGS. 9A and 9B, the mount 910 may take the form of a strap or band 920 that can be worn around the wrist (or some other part) of the body. Further, the mount 910 may be an adhesive substrate for adhering the payload delivering and/or blood-accessing device 900 to the body of a wearer.

A housing 930 is disposed on the mount 910 such that it can be positioned on the body. A contact surface 940 of the housing 930 is intended to be mounted facing to the external body surface. The housing 930 may include sensors for detecting one or more physiological properties of the wearer (e.g., a pulse, a blood oxygenation, a galvanic skin response). The contact surface 940 additionally includes a number of concave depressions 950. Each concave depression 950 corresponds to a payload delivering and/or blood-accessing section of the device 900 that can be operated to drive a hollow needle, through the concave depression (e.g., through a seal of the device and/or through a channel of the device configured to allow the passage of the needle), into skin of a wearer, to deliver a payload into the skin of the wearer through the hollow needle, and subsequently to retract the needle from the skin. Further, each section is configured to receive blood responsively emitted from the skin (e.g., by wicking, capillary action, application of suction, or some other means) and to store, detect a property of, or otherwise interact with the received blood.

The housing 930 could be configured to be water-resistant and/or water-proof. That is, the housing 930 could be configured to include sealants, adhesives, gaskets, welds, transparent windows, apertures, press-fitted seams, and/or other joints such that the housing 930 is resistant to water entering an internal volume or volumes of the housing 930 when the housing 930 is exposed to water. The housing 930 could further be water-proof, i.e., resistant to water entering an internal volume or volumes of the housing 930 when the housing 930 is submerged in water. For example, the housing 930 could be water-proof to a depth of 1 meter, i.e., configured to resist water entering an internal volume or volumes of the housing 930 when the housing 930 is submerged to a depth of 1 meter.

The wearable device 900 may also include a user interface 990 via which the wearer of the device may receive one or more recommendations or alerts generated either from a remote server or other remote computing device, or from a processor within the device. The alerts could be any indication that can be noticed by the person wearing the wearable device 900. For example, the alert could include a visual component (e.g., textual or graphical information on a display), an auditory component (e.g., an alarm sound), and/or tactile component (e.g., a vibration). Further, the user interface 990 may include a display 992 where a visual indication of the alert or recommendation may be displayed. The display 992 may further be configured to provide an indication of a measured hemodynamic property of blood accessed from the body of the wearer using the device (e.g., to provide an indication of a blood glucose level of the wearer's blood).

Further, the user interface 990 may include one or more buttons 994 for accepting inputs from the wearer. For example, the buttons 994 may be configured to change the text or other information visible on the display 992. The buttons 994 may be configured to accept inputs for controlling aspects of the data collection system, such as initiating a measurement period (e.g., causing the device 900 to access blood of the wearer by driving a needle into skin or according to some other method), initiating a delivery of a payload (e.g., a fluid containing insulin) into skin of the wearer, inputs indicating the wearer's current health state (i.e., normal, migraine, shortness of breath, heart attack, fever, "flu-like" symptoms, food poisoning, etc.), or inputs indicating the wearer's activities (e.g., eating a meal, taking a medication).

Note that example devices herein are configured to be mounted to a wrist of a wearer. However, the embodiments described herein could be applied to other body parts (e.g., an ankle, a thigh, a chest, an abdomen, a forehead, a thigh, a finger), or to detect hematological properties or other physiological properties in other environments. For example, embodiments described herein could be applied to detect one or more properties in a target environment (e.g., a natural environment, an environment of an industrial, pharmaceutical, or water treatment process).

Payload-delivering and/or blood-accessing sections of example devices 900, 800 could be single-use; for example, an injector of one or more sections could ignite a limited supply of a propellant and/or wherein suction is provided for/in a section by a single evacuated volume. In such examples, such single and/or limited-use payload delivering and/or blood-accessing sections could be configured to be a removable and/or replaceable element of the device 900/800. Wearable 900 and/or handheld 800 devices could be configured to operate single and/or limited-use payload delivering and/or blood-accessing sections of such a removable and/or replaceable element to access a number of samples of blood from skin (e.g., at respective specified points in time) and/or to deliver a number of different payload and/or amounts of a fluid or otherwise non-discrete payload. Once the body-mountable 900, handheld 800, or otherwise configured device has operated all of the sections of the removable and/or replaceable element, the removable and/or replaceable element could be removed from the body-mountable 900, handheld 800, or otherwise configured device and replaced. In some examples, this could include operating one or more injectors, suction sources, and/or other components of the removable and/or replaceable element (e.g., via an electrical connector, an optical receiver/transmitter, and/or electronics). Additionally or alternatively, the body-mountable 900, handheld 800, or otherwise configured device could operate the removable and/or replaceable element using other means, e.g., by igniting propellant of the removable and/or replaceable element by heating the propellant using a laser of the body-mountable 900, handheld 800, or otherwise configured device.

In some examples, the removed removable and/or replaceable element could be configured to store blood, and blood stored in the removed removable and/or replaceable element could be presented to a sensing device for analysis (e.g., the removed removable and/or replaceable element could be sent via post to a sensing device at a laboratory that is remote from a user of the body-mountable 900, handheld 800, or otherwise configured device). For example, samples of blood stored within the removable and/or replaceable element could be accessed via ports of the removable and/or replaceable element.

Payload-delivering and/or blood-accessing devices and other embodiments as described herein can include a variety of components configured in a variety of ways. Devices described herein could include electronics including a variety of different components configured in a variety of ways to enable applications of the wearable device. The electronics could include controllers, amplifiers, switches, display drivers, touch sensors, wireless communications chipsets (e.g., Bluetooth radios or other radio transceivers and associated baseband circuitry to enable wireless communications between the wearable device and some other system(s)), or other components. The electronics could include a controller configured to operate one or more sensors, injectors, reservoirs, suction sources, and/or components of a payload-delivering and/or blood-accessing device to deliver a fluid, object, or other payload into the body, to detect one or more hematological or other properties of a body, and/or to access and store or otherwise interact with blood from within and/or beneath skin of the body. The controller could include a processor configured to execute computer-readable instructions (e.g., program instructions stored in data storage of the wearable device) to enable applications of the device. The electronics can include additional or alternative components according to an application of the device.

Wearable or otherwise-configured payload-delivering and/or blood-accessing devices as described herein could include one or more user interfaces. A user interface could include a display configured to present an image to a user and to detect one or more finger presses of a user on the interface. The controller or some other component(s) of the electronics could operate the user interface to provide information to a wearer or other user of the device and to enable the wearer or other user to affect the operation of the device, to determine some property of the device and/or of the user of the device (e.g., a hematological property of blood and/or a health state of a user of the device), or to provide some other functionality or application to the wearer and/or user. As one example, the user could press an indicated region of the user interface to indicate that the device should begin logging detected medical information about the user. Other indicated information, changes in operation of the device, or other functions and applications of the user interface are anticipated.

Note that the embodiments illustrated in the Figures are illustrative examples and not meant to be limiting. Alternative embodiments, including more or fewer components in alternative configurations are anticipated. A wearable, handheld, body-mountable, desktop, or otherwise configured device could include multiple housings or other such assemblies each containing some set of components to enable applications of such a device. A payload-delivering and/or blood-accessing device as described herein could be configured to perform a variety of functions and to enable a variety of applications. Payload-delivering and/or blood-accessing devices could be configured to operate in concert with other devices or systems; for example, payload-delivering and/or blood-accessing devices could include a wireless communication interface configured to transmit data indicative of one or more properties of the blood of a wearer of the wearable device. Other embodiments, operations, configurations, and applications of a blood-accessing device as described herein are anticipated.

FIG. 10 is a simplified schematic of a system including one or more wearable payload-delivering and/or blood-accessing devices 1000. The one or more wearable devices 1000 may be configured to transmit data via a communication interface 1010 over one or more communication networks 1020 to a remote server 1030. In one embodiment, the communication interface 1010 includes a wireless transceiver for sending and receiving communications to and from the server 1030. In further embodiments, the communication interface 1010 may include any means for the transfer of data, including both wired and wireless communications. For example, the communication interface may include a universal serial bus (USB) interface or a secure digital (SD) card interface. Communication networks 1020 may be any one of may be one of: a plain old telephone service (POTS) network, a cellular network, a fiber network and a data network. The server 1030 may include any type of remote computing device or remote cloud computing network. Further, communication network 1020 may include one or more intermediaries, including, for example wherein the wearable device 1000 transmits data to a mobile phone or other personal computing device, which in turn transmits the data to the server 1030.

In some examples, multiple wearable devices 1000 could be configured to deliver fluid or other payloads into skin of, to access blood from and/or detect multiple hematological or other properties of a single wearer. For example, the single wearer could wear or otherwise operate two or more wearable devices 1000 to measure respective hematological or other physiological properties from respective two or more portions of the body of the wearer (e.g., respective portions of subsurface vasculature of the wearer) and/or during different periods of time (e.g., the wearable devices 1000 used by the wearer could be limited-use devices, e.g., each including a discrete number of single-use blood-accessing sections).

In addition to receiving communications from the wearable device 1000, such as collected hematological properties or other collected physiological properties and data regarding health state as input by the user and/or one or more properties of a wearer detected using a sensor disposed in the wearable device 1000, the server may also be configured to gather and/or receive either from the wearable device 1000 or from some other source, information regarding a wearer's overall medical history, environmental factors and geographical data. For example, a user account may be established on the server for every wearer that contains the wearer's medical history. Moreover, in some examples, the server 1030 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the hematological property data and the indicated health state of the user. From this information, the server may be configured to derive an indication of the effectiveness of the drug or treatment. For example, if a drug is intended to control a blood sugar of a wearer and the wearer of the device does not indicate that they are experiencing nausea, lightheadedness, or other sequelae after beginning a course of treatment with the drug, the server may be configured to derive an indication that the drug is effective for that wearer.

Further, some embodiments of the system may include privacy controls which may be automatically implemented or controlled by the wearer of the device. For example, where a wearer's collected hematological property data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and hematological properties, collected from his or her device may only be used for generating an individual baseline and recommendations in response to collection and comparison of his or her own data and may not be used in generating a population baseline or for use in population correlation studies.

IV. EXAMPLE ELECTRONICS

Figure 11:
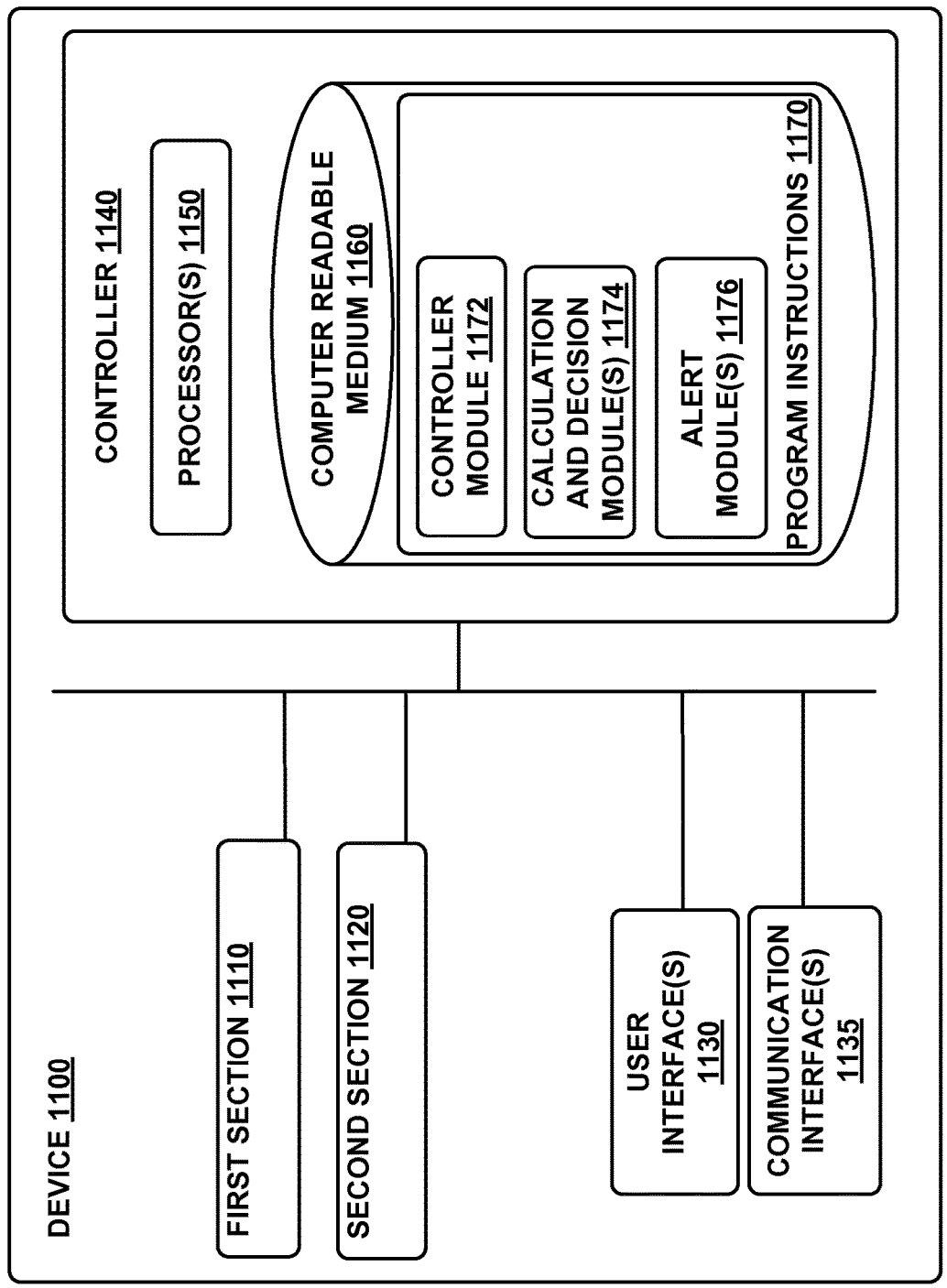
FIG. 11 is a functional block diagram of an example device.

FIG. 11 is a simplified block diagram illustrating the components of a device 1100, according to an example embodiment. Device 1100 may take the form of or be similar to one of the payload-delivering and/or blood-accessing devices 100, 200, 300, 400, 500, 600, 700, 900, 1000 shown in FIGS. 1A-B, 2A-E, 3A-B, 4A-B, 5A-B, 6A-B, 7A-B, 9A-B, and 10. However, device 1100 may also take other forms, such as an ankle, waist, or chest-mounted device. Device 1100 could also take the form of a device that is not configured to be mounted to a body. For example, device 1100 could take the form of a handheld device configured to be maintained in proximity to skin by a user or operator of the device 1000 or by a frame or other supporting structure, e.g., device 800. Device 1100 also could take other forms.

In particular, FIG. 11 shows an example of a device 1100 having first 1110 and second 1120 payload-delivering and/or blood-accessing sections, a user interface 1130, communication interface 1135 for transmitting data to a remote system, and a controller 1140. The components of the device 1100 may be disposed on a mount or on some other structure for mounting the device to enable stable collection of blood emitted from skin in response to penetration of the skin by one or more needles of the device 1100, for example, mounting to an external body surface where one or more portions of subsurface vasculature or other anatomical elements are readily accessible.

Controller 1140 may be provided as a computing device that includes one or more processors 1150. The one or more processors 1150 can be configured to execute computer-readable program instructions 1170 that are stored in the computer readable data storage 1160 and that are executable to provide the functionality of a device 1100 described herein.

The computer readable medium 1160 may include or take the form of one or more non-transitory, computer-readable storage media that can be read or accessed by at least one processor 1150. The one or more computer-readable storage media can include volatile and/or non-volatile storage components, such as optical, magnetic, organic or other memory or disc storage, which can be integrated in whole or in part with at least one of the one or more processors 1150. In some embodiments, the computer readable medium 1160 can be implemented using a single physical device (e.g., one optical, magnetic, organic or other memory or disc storage unit), while in other embodiments, the computer readable medium 1160 can be implemented using two or more physical devices.

First 1110 and second 1120 payload-delivering and/or blood-accessing sections could include any components configured to drive a needle into skin, to deliver a payload (e.g., a drug-containing fluid) into the skin, to subsequently retract the needle from the skin, to receive blood from the resulting puncture in the skin (e.g., by applying suction to the skin), and/or to perform other functions as described elsewhere herein. Payload-delivering and/or blood-accessing sections could include motors, piezoelectric transducers, solenoids, actuated valves, resistive heaters or other propellant-igniting components, or other components of an injector configured to drive a hollow needle into skin, to deliver a payload through the hollow needle into the skin, and/or to subsequently retract such a needle. Payload-delivering and/or blood-accessing sections 1110, 1120 could include blood-storage elements as described elsewhere herein to store blood for, e.g., later analysis. Payload-delivering and/or blood-accessing sections 1110, 1120 could include sensors configured to detect a variety of properties of blood drawn, wicked, suctioned, received, or otherwise accessed by the blood-accessing sections 1110, 1120. Payload-delivering and/or blood-accessing sections 1110, 1120 could include pumps or other elements (e.g., evacuated volumes) configured to provide suction (e.g., to draw skin toward and/or into concave depressions of the blood-accessing sections 1110, 1120, to draw blood from the skin into the device 1100, to direct blood within the device, 1100, e.g., to one or more sensors, blood-storage elements, or other components of the device 1100). The device 1100 could include additional (or fewer) payload-delivering and/or blood-accessing sections. The payload-delivering and/or blood-accessing sections 1110, 1120 could be similarly or differently configured. The payload-delivering and/or blood-accessing sections 1110, 1120 could be part of a removable and/or replaceable portion of the device 1100. The device 1100 may include further sensors (not shown), e.g., heart rate sensors, galvanic skin response sensors, pulse oximeters, or other sensors configured to detect one or more properties of the body of a user and/or of the environment of the device 1100.

The program instructions 1170 stored on the computer readable medium 1160 may include instructions to perform any of the methods described herein. For instance, in the illustrated embodiment, program instructions 1170 include a controller module 1172, calculation and decision module 1174 and an alert module 1176.

Calculation and decision module 1174 may include instructions for operating the payload-delivering and/or blood-accessing sections 1110, 1120 and analyzing data generated by the payload-delivering and/or blood-accessing sections 1110, 1120 (e.g., by sensors thereof) to determine one or more hematological properties of blood or other information (e.g., health states) of a body of a user of the device 1100, such as a blood glucose level at a number of points in time. Calculation and decision module 1174 can additionally include instructions for analyzing the data to determine if a medical condition or other specified condition is indicated, or other analytical processes relating to the environment proximate to the device 1100 (e.g., based on information generated by additional sensors of the device 1100). In particular, the calculation and decision module 1174 may include instructions for operating the first 1110 and second 1120 payload-delivering and/or blood-accessing sections to deliver a payload (e.g., a fluid containing a drug) at a specified point or points in time, to deliver a specified amount of the payload, to deliver a specified payload of a discrete set of possible payloads (e.g., a set of fluids containing different drugs), or according to some other application. The calculation and decision module 1174 may additionally include instructions for operating the first 1110 and second 1120 payload-delivering and/or blood-accessing sections to access blood (e.g., for operating resistive heating elements of the payload-delivering and/or blood-accessing sections 1110, 1120 to ignite propellant and drive respective needles into skin) at respective specified points in time (e.g., points in time while a wearer sleeps, points in time during the week).

The controller module 1172 can also include instructions for operating a user interface 1130. For example, controller module 1172 may include instructions for displaying data collected by the payload-delivering and/or blood-accessing sections 1110, 1120 and analyzed by the calculation and decision module 1174, or for displaying one or more alerts generated by the alert module 1176. Controller module 1172 may include instructions for displaying data related to a detected hematological property of accessed blood and/or a determined health state of a user. Further, controller module 1172 may include instructions to execute certain functions based on inputs accepted by the user interface 1130, such as inputs accepted by one or more buttons disposed on the user interface (e.g., to operate one or both of the payload-delivering and/or blood-accessing sections 1110, 1120 to deliver a payload into skin, to access blood from a user and/or to detect one or more properties of the accessed blood in response to an input from the user).

Communication platform 1135 may also be operated by instructions within the controller module 1172, such as instructions for sending and/or receiving information via a wireless antenna, which may be disposed on or in the device 1100. The communication interface 1135 can optionally include one or more oscillators, mixers, frequency injectors, etc. to modulate and/or demodulate information on a carrier frequency to be transmitted and/or received by the antenna. In some examples, the device 1100 is configured to indicate an output from the processor by modulating an impedance of the antenna in a manner that is perceivable by a remote server or other remote computing device.

The program instructions of the calculation and decision module 1174 may, in some examples, be stored in a computer-readable medium and executed by a processor located external to the device 1100. For example, the device 1100 could be configured to collect certain data regarding hematological properties from the user and then transmit the data to a remote server, which may include a mobile device, a personal computer, the cloud, or any other remote system, for further processing.

The computer readable medium 1160 may further contain other data or information, such as medical and health history of a user of the device 1100, a drug treatment regimen determined for a user of the device 1100, that may be useful in operating the device 1100 and/or determining whether a medical condition or some other specified condition is indicated. Further, the computer readable medium 1160 may contain data corresponding to certain physiological parameter baselines, above or below which a medical condition is indicated. The baselines may be pre-stored on the computer readable medium 1160, may be transmitted from a remote source, such as a remote server, or may be generated by the calculation and decision module 1174 itself. The calculation and decision module 1174 may include instructions for generating individual baselines for the user of the device 1100 based on data collected based on a certain number of blood samples accessed using blood-accessing elements (e.g., 1110, 1120) of the device 1100. Baselines may also be generated by a remote server and transmitted to the device 1100 via communication interface 1130. The calculation and decision module 1174 may also, upon determining that a medical or other emergency condition is indicated, generate one or more recommendations for the user of the device 1100 based, at least in part, on consultation of a clinical protocol. Such recommendations may alternatively be generated by the remote server and transmitted to the device 1100.

In some examples, the collected hematological property data, baseline profiles, health state information input by device users and generated recommendations and clinical protocols may additionally be input to a cloud network and be made available for download by a user's physician. Trend and other analyses may also be performed on the collected data, such as hemodynamic property data and health state information, in the cloud computing network and be made available for download by physicians or clinicians.

Further, hematological property and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular user's response to a drug or therapy. Based on this data, a physician or clinician may be able to tailor a drug treatment to suit an individual's needs.

In response to a determination by the calculation and decision module 1174 that a medical or other specified condition is indicated (e.g., that a user is hyperglycemic or hypoglycemic, based on a detected glucose level of blood accessed from the body of the user), the alert module 1176 may generate an alert via the user interface 1130. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, operate one or both of the payload-delivering elements 1110, 1120 to deliver a dose of a pharmaceutical (e.g., insulin), seek immediate medical attention, or administer a medication.

V. EXAMPLE METHODS

Figure 12:
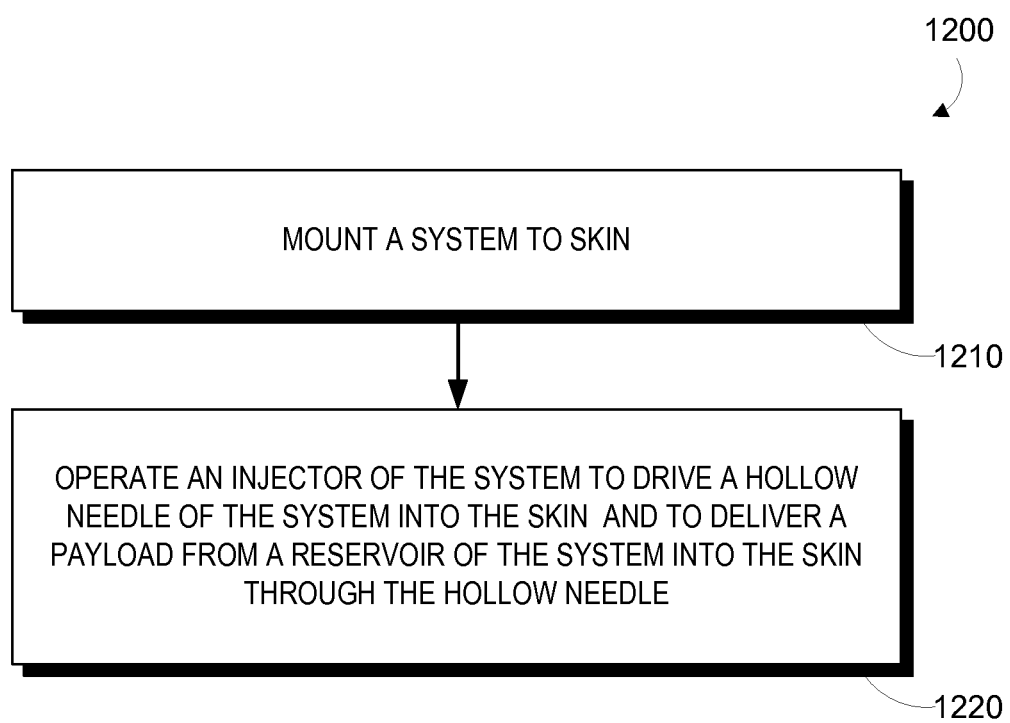
FIG. 12 is a flowchart of an example method.

FIG. 12 is a flowchart of a method 1200 for operating a payload-delivering and/or blood-accessing system. The operated system includes: (i) a hollow needle that includes a channel and that is configured to penetrate skin, (ii) a reservoir that contains a fluid, a gel, one or more solid or semi-solid objects, or some other payload, (iii) an injector, and (iv) a controller. The method 1200 includes mounting the system to skin (1210). The system could be a wearable device and mounting the system to skin (1210) could include mounting the system to and/or around a part of a body using a strap, adhesive, or some other means. The system could be a handheld device and mounting the system to skin (1210) could include manually or otherwise positioning the system proximate skin. The system could be a desktop device, a wall- or ceiling-mounted device, or some other form of stationary device and mounting the system to skin (1210) could include positioning a body part having the skin (e.g., a wrist, and arm) proximate the system.

The method 1200 also includes operating the injector to drive the hollow needle into the skin to form a puncture and delivering a payload from the reservoir into skin through the channel of the hollow needle (1220). This could include the controller operating the injector at a specified point in time and/or in response to a command (e.g., a command received through a user interface of the system, a command generated by the system in response to detecting that skin is present proximate the system, a command generated by a remote system in communication with the payload-delivering and/or blood-accessing system). Operating the injector (1220) could additionally include drawing blood from the formed puncture in the skin into the system using suction provided by a suction source. Operating the injector (1220) could include igniting a propellant, e.g., by heating the propellant using a resistive heating element. Additionally or alternatively, operating the injector (1220) could include operating a motor, solenoid, piezoelectric transducer, or other elements of the system and/or of the injector.

The system could include one or more sensors configured to detect one or more properties of blood accessed by and drawn into the system and the method 1200 could include operating the sensor to detect the one or more properties of the blood (e.g., to detect a glucose concentration in the blood). Additionally or alternatively, the system could include one or more blood storage elements configured to receive and store blood accessed by the system and the method 1200 could include storing the accessed blood. The method 1200 could further include providing blood stored by the blood storage element to a sensing device and operating the sensing device to detect a property of the blood provided to the sensing device. In some examples, one or more elements, sections, or portions of the system (e.g., a section configured to drive a needle into skin, to deliver a payload through the hollow needle into the skin, to subsequently retract the needle, and/or to apply suction to the skin to draw blood into the section) could be removable, and the method 1200 could include removing and replacing such elements, sections, or portions subsequent to operating such elements, sections, or portions to access blood from skin.

The method 1200 could include additional or alternative steps. The method 1200 could include heating, applying suction to, or otherwise preparing a portion of skin to emit blood in response to being pierced by a needle of the system. In some examples, the method 1200 could include transmitting (e.g., wirelessly transmitting, transmitting via a Bluetooth wireless link, transmitting via a cable, transmitting via the internet or some other network) information indicative of a detected hematological property of blood accessed by the system. In some examples, the method 1200 could include determining a health state of the user based on a hematological property detected from blood accessed by the system. In some examples, the method 1200 could include indicating a detected hematological properties or other information about the operation of the system to a user via a user interface of the system and/or indicating such information to a remote system (e.g., to a physician's computer, via a wireless or other communications link).

The example method 1200 illustrated in FIG. 12 is meant as an illustrative, non-limiting example. Additional or alternative elements of the method and additional or alternative components of the system are anticipated, as will be obvious to one skilled in the art.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   a housing;
   a seal disposed on a surface of the housing;
   a first chamber disposed within the housing, wherein the first chamber contains a sealant layer;
   a hollow needle disposed in the first chamber and configured to pierce the sealant layer, wherein the hollow needle comprises a first channel;
   a reservoir, wherein the reservoir contains a payload;
   an injector, wherein the injector is operable to drive the hollow needle through the seal to form a hole in the seal and thereafter into skin to form a puncture in the skin, such that the payload is delivered from the reservoir into the skin via the first channel;
   a second chamber disposed within the housing;
   a second channel coupled to the second chamber, wherein the second channel is formed by the seal and the housing;
   a suction source configured to provide suction, wherein the suction provided by the suction source is configured to draw blood from the puncture formed in the skin into the second chamber via the hole formed in the seal and the second channel;
   a sensor; and
   a controller, wherein the controller is configured to perform controller functions including:
      operating the sensor to detect information about an environment of the system;
      determining that a specified condition has occurred based on the information about the environment of the system detected using the sensor; and
      responsive to determining that the specified condition has occurred, operating the injector to drive the hollow needle through the seal and into the skin to deliver the payload into the skin via the first channel.

2. The system of claim 1, wherein the injector comprises:
   a piston disposed in the first chamber, wherein the hollow needle is coupled to the piston, wherein the piston comprises the reservoir, and wherein the piston is configured to slidably move within the first chamber; and
   a propellant, wherein the propellant is configured to slidably move the piston within the first chamber to drive the hollow needle through the seal and into skin.

3. The system of claim 1, wherein the seal comprises a concave depression, wherein the injector is configured to drive the hollow needle into skin proximate the concave depression, and wherein the suction provided by the suction source is configured to suction the skin into the concave depression.

4. The system of claim 1, wherein the sensor is disposed in the second channel, and wherein the sensor is configured to detect a property of blood to which the sensor is exposed.

5. The system of claim 1, wherein the payload contained by the reservoir comprises heparin.

6. The system of claim 1, wherein determining that a specified condition has occurred comprises determining that a specified point in time has been reached.

7. The system of claim 1, wherein the suction source comprises an evacuated volume in the second chamber.

8. The system of claim 1, further comprising a spring disposed within the first chamber, wherein the spring is configured to retract the hollow needle from the skin.

* * * * *